United States Patent
Hong et al.

(10) Patent No.: US 7,959,626 B2
(45) Date of Patent: Jun. 14, 2011

(54) TRANSMURAL ABLATION SYSTEMS AND METHODS

(75) Inventors: Jinback Hong, Maple Grove, MN (US); David E. Francischelli, Anoka, MN (US); Mark T. Stewart, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 997 days.

(21) Appl. No.: 11/780,911

(22) Filed: Jul. 20, 2007

(65) Prior Publication Data

US 2008/0015562 A1  Jan. 17, 2008

Related U.S. Application Data

(63) Continuation-in-part of application No. 10/923,178, filed on Aug. 20, 2004, now Pat. No. 7,250,048, which is a continuation-in-part of application No. 10/364,553, filed on Feb. 11, 2003, now Pat. No. 6,989,010, which is a continuation-in-part of application No. 10/132,379, filed on Apr. 24, 2002, now Pat. No. 6,648,883.

(60) Provisional application No. 60/287,202, filed on Apr. 26, 2001, provisional application No. 60/832,242, filed on Jul. 20, 2006, provisional application No. 60/923,365, filed on Apr. 13, 2007.

(51) Int. Cl.
*A61B 18/18* (2006.01)

(52) U.S. Cl. .......................................... 606/34; 606/38

(58) Field of Classification Search ................ 606/34, 606/37–38
See application file for complete search history.

(56) References Cited

U.S. PATENT DOCUMENTS

| | | |
|---|---|---|
| 3,736,936 A | 6/1973 | Basiulis et al. |
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |
| 3,910,277 A | 10/1975 | Zimmer |

(Continued)

FOREIGN PATENT DOCUMENTS

EP  0136855  11/1989

(Continued)

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

(Continued)

*Primary Examiner* — Roy D Gibson
*Assistant Examiner* — Jaymi Della

(57) ABSTRACT

A method of applying ablation energy to achieve transmurality including applying ablation energy at a starting power to a tissue site and monitoring the impedance of the tissue site. The power applied to the tissue site can be increased in response to detection of a power plateau or application of a first power for a minimum time according to some embodiments. A power applied to the tissue site can be reduced in response to an increase in impedance according to some embodiments. Transmurality can be indicated in response to a transmurality plateau following a rise in impedance according to some embodiments.

12 Claims, 13 Drawing Sheets

U.S. PATENT DOCUMENTS

| | | |
|---|---|---|
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |
| 4,377,168 A | 3/1983 | Rzasa et al. |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,936,281 A | 6/1990 | Stasz |
| 4,946,460 A | 8/1990 | Merry et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelna |
| 5,100,388 A | 3/1992 | Behl et al. |
| 5,108,390 A | 4/1992 | Potocky et al. |
| 5,147,355 A | 9/1992 | Friedman et al. |
| 5,178,133 A | 1/1993 | Pena |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,233,515 A | 8/1993 | Cosman |
| 5,254,116 A | 10/1993 | Baust et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,300,068 A | 4/1994 | Rosar et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowle |
| 5,334,181 A | 8/1994 | Rubinsky et al. |
| 5,334,193 A | 8/1994 | Nardella |
| 5,341,807 A | 8/1994 | Nardella |
| 5,342,357 A | 8/1994 | Nardella |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,385,148 A | 1/1995 | Lesh et al. |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,423,807 A | 6/1995 | Milder |
| 5,423,811 A | 6/1995 | Imran et al. |
| 5,427,119 A | 6/1995 | Swartz et al. |
| 5,431,649 A | 7/1995 | Mulier et al. |
| 5,433,708 A | 7/1995 | Nichols |
| 5,435,308 A | 7/1995 | Gallup et al. |
| 5,437,651 A | 8/1995 | Todd et al. |
| 5,437,664 A | 8/1995 | Cohen et al. |
| 5,443,463 A | 8/1995 | Stern et al. |
| 5,443,470 A | 8/1995 | Stern et al. |
| 5,450,843 A | 9/1995 | Moll et al. |
| 5,452,582 A | 9/1995 | Longsworth |
| 5,452,733 A | 9/1995 | Sterman et al. |
| 5,456,662 A | 10/1995 | Edwards et al. |
| 5,456,682 A | 10/1995 | Edwards et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,540,681 A | 7/1996 | Strul et al. |
| 5,540,684 A | 7/1996 | Hassler, Jr. |
| 5,542,928 A | 8/1996 | Evans et al. |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,558,671 A | 9/1996 | Yates |
| 5,560,362 A | 10/1996 | Sliwa, Jr. et al. |
| 5,562,720 A | 10/1996 | Stern et al. |
| 5,562,721 A | 10/1996 | Marchlinski et al. |
| 5,569,241 A | 10/1996 | Edwards |
| 5,571,088 A | 11/1996 | Lennox et al. |
| 5,571,215 A | 11/1996 | Sterman et al. |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,584,872 A | 12/1996 | LaFontaine et al. |
| 5,588,432 A | 12/1996 | Crowley |
| 5,590,657 A | 1/1997 | Cain et al. |
| 5,595,183 A | 1/1997 | Swanson et al. |
| 5,607,462 A | 3/1997 | Imran |
| 5,609,151 A | 3/1997 | Mulier et al. |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,653,692 A | 8/1997 | Masterson et al. |
| 5,656,029 A | 8/1997 | Imran et al. |
| 5,658,278 A | 8/1997 | Imran et al. |
| 5,671,747 A | 9/1997 | Connor |
| 5,673,695 A | 10/1997 | McGee et al. |
| 5,673,704 A | 10/1997 | Marchlinski et al. |
| 5,676,662 A | 10/1997 | Fleischhacker et al. |
| 5,676,692 A | 10/1997 | Sanghvi et al. |
| 5,676,693 A | 10/1997 | LaFontaine |
| 5,678,550 A | 10/1997 | Bassen et al. |
| 5,680,860 A | 10/1997 | Imran |
| 5,681,278 A | 10/1997 | Igo et al. |
| 5,681,308 A | 10/1997 | Edwards et al. |
| 5,687,723 A | 11/1997 | Avitall |
| 5,687,737 A | 11/1997 | Branham et al. |

| Patent | Date | Inventor |
|---|---|---|
| 5,688,267 A | 11/1997 | Panescu et al. |
| 5,690,611 A | 11/1997 | Swartz et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,713,896 A | 2/1998 | Nardella |
| 5,713,942 A | 2/1998 | Stern |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Larnard |
| 5,722,402 A | 3/1998 | Swanson et al. |
| 5,722,975 A | 3/1998 | Edwards et al. |
| 5,725,524 A | 3/1998 | Mulier et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,733,281 A | 3/1998 | Nardella |
| 5,735,280 A | 4/1998 | Sherman et al. |
| 5,735,290 A | 4/1998 | Sterman et al. |
| 5,749,869 A | 5/1998 | Lindenmeier et al. |
| 5,755,760 A | 5/1998 | Maguire et al. |
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,797,960 A | 8/1998 | Stevens et al. |
| 5,800,428 A | 9/1998 | Nelson et al. |
| 5,800,482 A | 9/1998 | Pomeranz et al. |
| 5,807,395 A | 9/1998 | Mulier et al. |
| 5,810,802 A | 9/1998 | Panescu et al. |
| 5,827,216 A | 10/1998 | Igo et al. |
| 5,836,874 A | 11/1998 | Swanson et al. |
| 5,836,947 A | 11/1998 | Fleischman et al. |
| 5,840,030 A | 11/1998 | Ferek-Petric et al. |
| 5,844,349 A | 12/1998 | Oakley et al. |
| 5,846,187 A | 12/1998 | Wells et al. |
| 5,846,191 A | 12/1998 | Wells et al. |
| 5,849,028 A | 12/1998 | Chen |
| 5,868,739 A | 2/1999 | Lindenmeier et al. |
| 5,871,523 A | 2/1999 | Fleischman et al. |
| 5,871,525 A | 2/1999 | Edwards et al. |
| 5,873,845 A | 2/1999 | Cline et al. |
| 5,876,398 A | 3/1999 | Mulier et al. |
| 5,876,399 A | 3/1999 | Chia et al. |
| 5,879,295 A | 3/1999 | Li et al. |
| 5,879,296 A | 3/1999 | Ockuly et al. |
| 5,881,732 A | 3/1999 | Sung et al. |
| 5,882,346 A | 3/1999 | Pomeranz et al. |
| 5,885,278 A | 3/1999 | Fleischman |
| 5,888,198 A | 3/1999 | Eggers et al. |
| 5,891,095 A | 4/1999 | Eggers et al. |
| 5,893,848 A | 4/1999 | Negus et al. |
| 5,895,417 A | 4/1999 | Pomeranz et al. |
| 5,897,533 A | 4/1999 | Glickman |
| 5,897,552 A | 4/1999 | Edwards et al. |
| 5,897,553 A | 4/1999 | Mulier et al. |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,902,328 A | 5/1999 | LaFontaine et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,906,613 A | 5/1999 | Mulier et al. |
| 5,908,029 A | 6/1999 | Knudson et al. |
| 5,913,854 A | 6/1999 | Maguire et al. |
| 5,913,856 A | 6/1999 | Chia et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,927,284 A | 7/1999 | Borst et al. |
| 5,928,191 A | 7/1999 | Houser et al. |
| 5,931,810 A | 8/1999 | Grabek |
| 5,931,835 A | 8/1999 | Mackey |
| 5,931,848 A | 8/1999 | Saadat |
| 5,954,661 A | 9/1999 | Greenspon et al. |
| 5,954,717 A | 9/1999 | Behl et al. |
| 5,957,961 A | 9/1999 | Maguire et al. |
| 5,971,980 A | 10/1999 | Sherman |
| 5,971,983 A | 10/1999 | Lesh |
| 5,976,128 A | 11/1999 | Schilling et al. |
| 5,993,447 A | 11/1999 | Blewett et al. |
| 6,007,499 A | 12/1999 | Martin et al. |
| 6,012,457 A | 1/2000 | Lesh |
| 6,016,811 A | 1/2000 | Knopp et al. |
| 6,033,399 A * | 3/2000 | Gines .............................. 606/38 |
| 6,042,556 A | 3/2000 | Beach et al. |
| 6,063,081 A | 5/2000 | Mulier |
| 6,071,279 A | 6/2000 | Whayne et al. |
| 6,080,149 A | 6/2000 | Huang et al. |
| 6,083,223 A | 7/2000 | Baker |
| 6,088,894 A | 7/2000 | Oakley |
| 6,096,037 A | 8/2000 | Mulier et al. |
| 6,112,123 A | 8/2000 | Kelleher et al. |
| 6,113,592 A | 9/2000 | Taylor |
| 6,117,101 A | 9/2000 | Diederich et al. |
| 6,120,496 A | 9/2000 | Whayne et al. |
| 6,142,992 A | 11/2000 | Cheng et al. |
| 6,142,993 A | 11/2000 | Whayne et al. |
| 6,142,994 A | 11/2000 | Swanson et al. |
| 6,152,920 A | 11/2000 | Thompson et al. |
| 6,161,543 A | 12/2000 | Cox et al. |
| 6,162,216 A | 12/2000 | Guziak et al. |
| 6,165,174 A | 12/2000 | Jacobs et al. |
| 6,179,834 B1 | 1/2001 | Buysse et al. |
| 6,183,468 B1 | 2/2001 | Swanson et al. |
| 6,183,469 B1 | 2/2001 | Thapliyal et al. |
| 6,217,528 B1 | 4/2001 | Koblish et al. |
| 6,217,576 B1 | 4/2001 | Tu et al. |
| 6,224,592 B1 | 5/2001 | Eggers et al. |
| 6,231,518 B1 | 5/2001 | Grabek et al. |
| 6,235,020 B1 | 5/2001 | Cheng et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,393 B1 | 5/2001 | Mulier et al. |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,128 B1 | 6/2001 | Knopp et al. |
| 6,270,471 B1 | 8/2001 | Hechel et al. |
| 6,293,943 B1 | 9/2001 | Panescu et al. |
| 6,296,619 B1 | 10/2001 | Brisken et al. |
| 6,296,636 B1 | 10/2001 | Cheng et al. |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,322,558 B1 | 11/2001 | Taylor et al. |
| 6,325,797 B1 | 12/2001 | Stewart et al. |
| 6,328,736 B1 | 12/2001 | Mulier |
| 6,332,881 B1 | 12/2001 | Carner et al. |
| 6,358,248 B1 | 3/2002 | Mulier et al. |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey et al. |
| 6,413,254 B1 | 7/2002 | Hissong et al. |
| 6,419,648 B1 | 7/2002 | Vitek et al. |
| 6,423,057 B1 | 7/2002 | He et al. |
| 6,425,867 B1 | 7/2002 | Vaezy et al. |
| 6,430,426 B2 | 8/2002 | Avitall |

| | | |
|---|---|---|
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,484,727 B1 | 11/2002 | Vaska et al. |
| 6,488,680 B1 | 12/2002 | Francischelli |
| 6,502,575 B1 | 1/2003 | Jacobs et al. |
| 6,508,815 B1 | 1/2003 | Strul et al. |
| 6,514,250 B1 | 2/2003 | Jahns |
| 6,527,767 B2 | 3/2003 | Wang et al. |
| 6,537,248 B2 | 3/2003 | Mulier |
| 6,537,272 B2 | 3/2003 | Christopherson et al. |
| 6,546,935 B2 | 4/2003 | Hooven |
| 6,558,382 B2 | 5/2003 | Jahns |
| 6,584,360 B2 | 6/2003 | Francischelli |
| 6,585,732 B2 | 7/2003 | Mulier |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,645,199 B1 | 11/2003 | Jenkins et al. |
| 6,648,883 B2 | 11/2003 | Francischelli |
| 6,656,175 B2 | 12/2003 | Francischelli |
| 6,663,627 B2 | 12/2003 | Francischelli |
| 6,692,450 B1 | 2/2004 | Coleman |
| 6,699,240 B2 | 3/2004 | Francischelli |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,807,968 B2 | 10/2004 | Francischelli |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 2001/0039419 A1 | 11/2001 | Francischelli et al. |
| 2002/0026186 A1 | 2/2002 | Woloszko et al. |
| 2002/0029036 A1 | 3/2002 | Goble et al. |
| 2003/0014047 A1 | 1/2003 | Woloszko et al. |
| 2003/0045872 A1 | 3/2003 | Jacobs |
| 2003/0144656 A1 | 7/2003 | Ocel |
| 2003/0191462 A1 | 10/2003 | Jacobs |
| 2003/0208193 A1 | 11/2003 | Van Wyk |
| 2003/0216724 A1 | 11/2003 | Jahns |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0095100 A1* | 5/2004 | Thompson ............... 322/32 |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0004567 A1* | 1/2005 | Daniel et al. ............... 606/50 |
| 2005/0010095 A1 | 1/2005 | Stewart |
| 2005/0033280 A1 | 2/2005 | Francischelli |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Chrisitian |

FOREIGN PATENT DOCUMENTS

| | | |
|---|---|---|
| EP | 0368532 | 12/1993 |
| WO | 94/24949 | 11/1994 |
| WO | 01/87172 | 11/2001 |

OTHER PUBLICATIONS

Gallagher et al., "Cryosurgical Ablation of Accessory Atrioventrical Connections: A Method for Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Technique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:206-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery, vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): 1-594. Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphiia: WB Saunders: 460-475, 1994.

Sueda et al., "Simple Left Atrial Procedure for Chronic Atrial Fibrillation Associated with Mitral Valve Disease," The Annals of Thoracic Surgery 62(6): 1796-1800, 1996.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," J of Thorac Cardiovasc Surg, 1991: 101: 584-593.

Nardella, "Radio Frequency Energy and Impedance Feedback," SPIE vol. 1068, Catheter Based Sensing and Imaging Technology (1989).

Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:250,I-675,#3946.

Sie et al., "Radiofrequency Ablation of Atrial Fibrillation in Patients Undergoing Valve Surgery," Circulation (Nov. 1997) 84:1450,#2519.

Jais et al., "Catheter Ablation for Paroxysmal Atrial Fibrillation: High Success Rates with Ablation in the Left Atrium," Circulation (Nov. 1996) 94.I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Supp 1):I-493, #2889.

Cox et al., "An 8½ Year Clinical Experience with Surgery for Atrial Fibrillation," Annals of Surgery, 1996;224 (3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

* cited by examiner

TIME TO FIRST POWER PLATEAU
(OVERALL n=208)

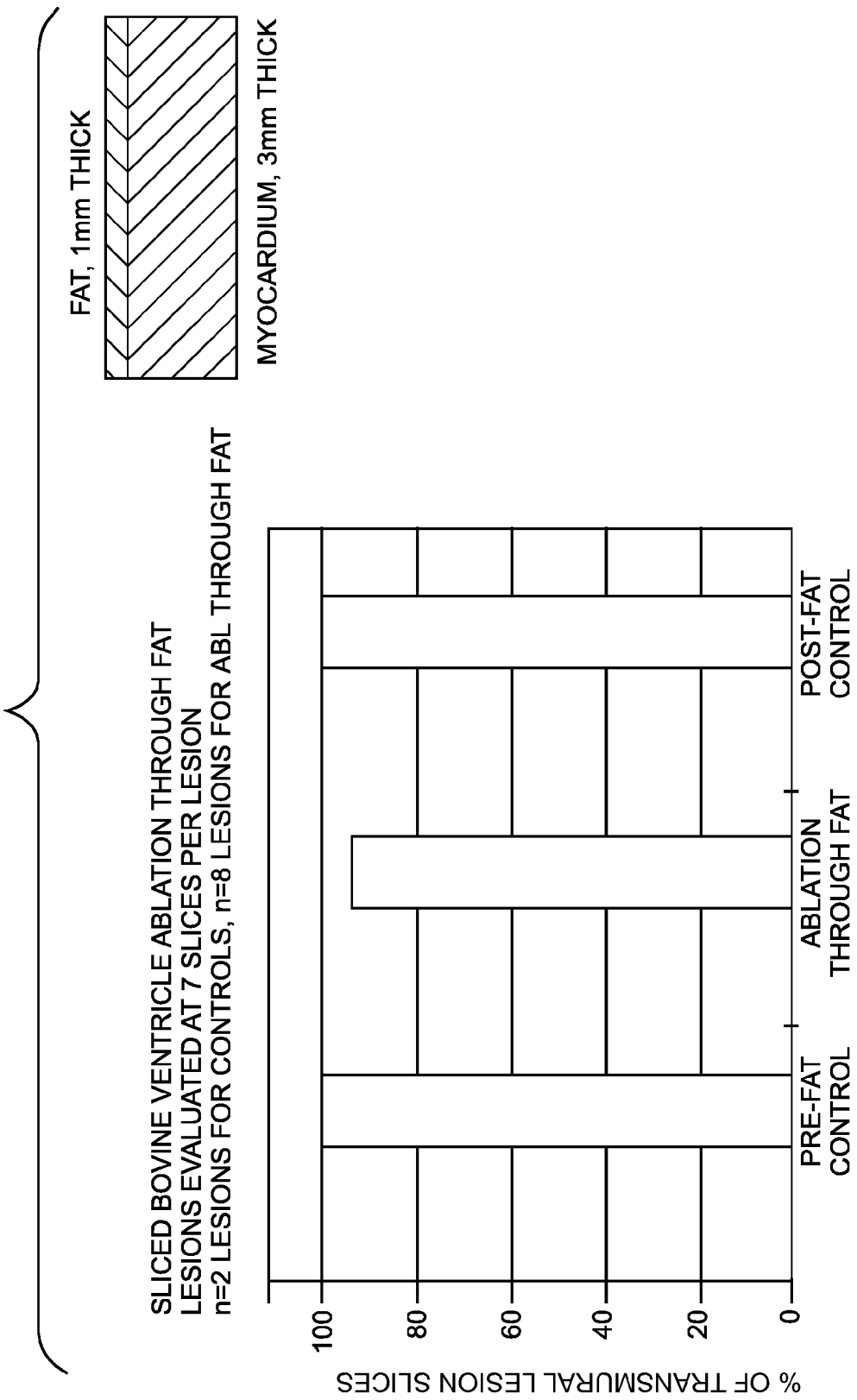

TRANSMURAL ABLATION SYSTEMS AND METHODS

CROSS-REFERENCE TO RELATED APPLICATIONS

This application is a continuation-in-part of U.S. patent application Ser. No. 10/923,178, filed Aug. 20, 2004, now U.S. Pat. No. 7,250,048, which is a continuation-in-part of U.S. patent application Ser. No. 10/364,553, filed Feb. 11, 2003, now U.S. Pat. No. 6,989,010, which is a continuation-in-part application of U.S. patent application Ser. No. 10/132,379, filed Apr. 24, 2002, now U.S. Pat. No. 6,648,883, which claims priority to Provisional U.S. Patent Application Ser. No. 60/287,202, filed Apr. 26, 2001, the contents of which are hereby incorporated by reference in their respective entireties.

This application also claims priority to U.S. Provisional Patent Application Ser. No. 60/832,242 filed Jul. 20, 2006, and U.S. Provisional Patent Application Ser. No. 60/923,365 filed Apr. 13, 2007, the contents of both of which are hereby incorporated by reference in their respective entireties.

FIELD

Embodiments of the invention related generally to systems and methods for ablating tissue, and more particularly, to systems and methods for performing transmural ablations.

BACKGROUND

The Maze procedure is a surgical treatment for patients with chronic atrial fibrillation that is resistant to other treatments. The Maze procedure uses incisions in the right and left atria to divide the atria into electrically isolated portions, which in turn results in an orderly passage of the depolarization wave front from the sino-atrial node to the atrial-ventricular node, while preventing reentrant wave front propagation. Although successful in treating atrial fibrillation, the Maze procedure can be quite complex and is currently performed by a limited number of highly skilled cardiac surgeons in conjunction with other open-heart procedures. As a result of the complexities of the Maze procedure, there has been an increased level of interest in procedures employing electrosurgical devices or other types of ablation devices, (e.g., thermal ablation, micro-wave ablation, radio frequency or RF ablation, and cryo-ablation) to ablate tissue along pathways approximating the incisions of the Maze procedure.

Three basic approaches have been used to create elongated lesions with electrosurgical devices. The first approach is to create a series of short lesions using a contact electrode, moving it along the surface of the organ wall to be ablated to create a linear lesion. This can be accomplished either by making a series of lesions, moving the electrode between lesions, or by dragging the electrode along the surface of the organ to be ablated and continuously applying ablation energy. The second approach to creation of elongated lesions is to use an elongated electrode and to place the elongated electrode along the desired line of lesion along the tissue. The third approach to creation of elongated lesions is to provide a series of electrodes and arrange the series of electrodes along the desired line of lesion. The electrodes may be activated individually or in sequence. In the case of multi-electrode devices, individual feedback regulation of ablated energy applied via the electrodes may also be employed.

In conjunction with the use of electrosurgical ablation devices, various control mechanisms have been developed to control the delivery of ablation energy to achieve the desired result of ablation (i.e., killing of cells at the ablation site, while leaving the basic structure of the organ to be ablated intact). Such control systems include measurement of temperature and impedance at or adjacent to the ablation site, as disclosed in U.S. Pat. No. 5,540,681, issued to Struhl, et al.

Additionally, there has been substantial work done toward assuring that the ablation procedure is complete, i.e., that the ablation extends through the thickness of the tissue to be ablated, before terminating application of ablation energy. This desired result is sometimes referred to as a "transmural" ablation. For example, detection of a desired drop in electrical impedance of the tissue being ablated at the electrode site as an indicator of transmurality is disclosed in U.S. Pat. No. 5,562,721 issued to Marchlinski et al. Alternatively, detection of an impedance rise or an impedance rise following an impedance fall is disclosed in U.S. Pat. No. 5,558,671 issued to Yates and U.S. Pat. No. 5,540,684 issued to Hassler, respectively.

Previous transmurality algorithms were fundamentally based on the concept of identifying a flat impedance curve or plateau in response to an increase in power of ablation energy output to determine transmurality. However, there are many situations in which the flattened impedance curve does not remain plateaued long enough for the algorithm to determine that the flattened impedance curve indicates transmurality. The ablation is allowed to continue, which can sometimes cause the impedance curve to rise as a result of increased temperature (this usually occurs in fatty, inhomogeneous, or thicker tissues). Therefore, ablation is not terminated until the detection of an impedance rise followed by a minimum time delay or by reaching the high impedance limit. This is an inefficient method for performing a transmural ablation and can result in over-ablation.

SUMMARY

In one embodiment, the invention provides a method of applying ablation energy to achieve transmurality at a tissue site including applying ablation energy at a first power to the tissue site, monitoring impedance of the tissue site, and reducing the ablation energy applied to the tissue site to a second power in response to a rise in impedance.

Other aspects of the invention will become apparent by consideration of the detailed description and accompanying drawings.

BRIEF DESCRIPTION OF THE DRAWINGS

FIG. 14 is a chart comparing lesion transmurality after ablating over fat for a previous algorithm versus an algorithm according to one embodiment of the invention.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Figure 1:
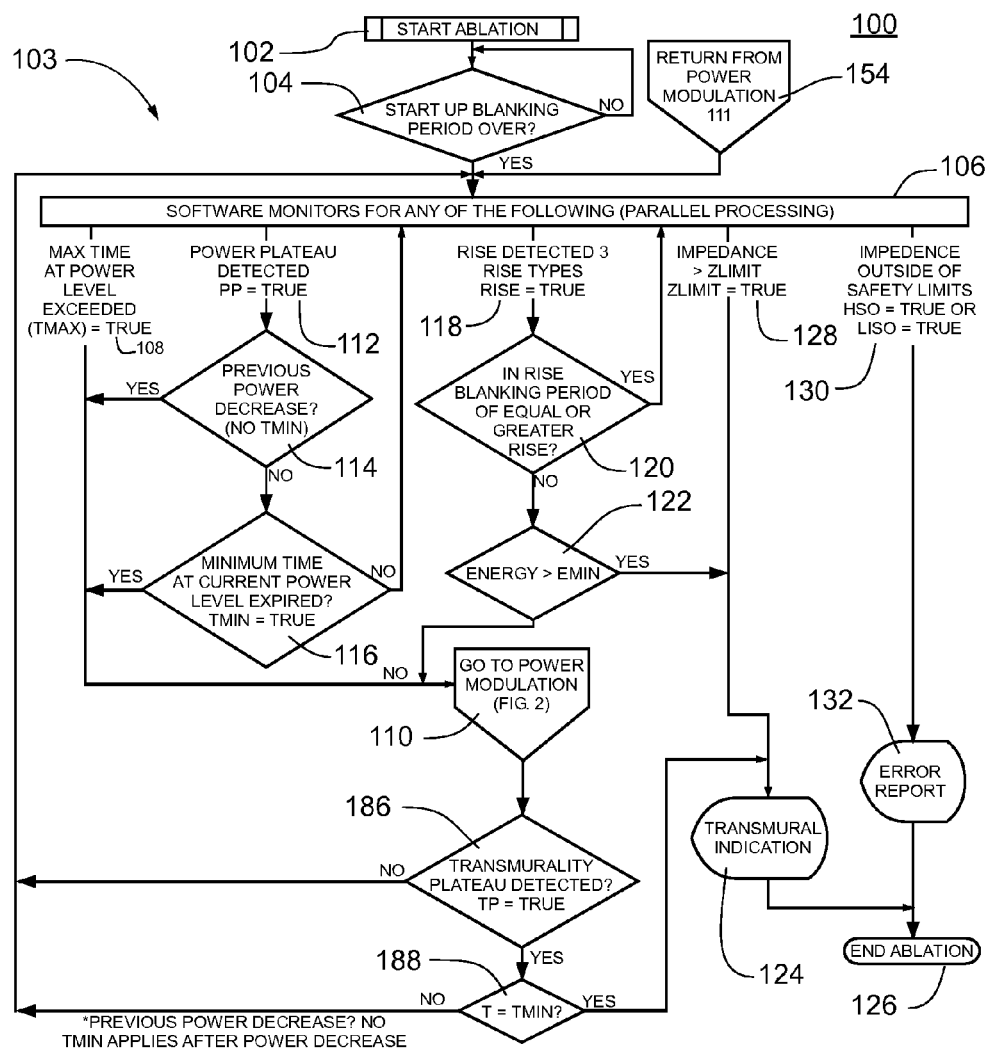
FIG. 1 is a flowchart depicting an algorithm for determining transmurality according to one embodiment of the invention.
Figure 2:
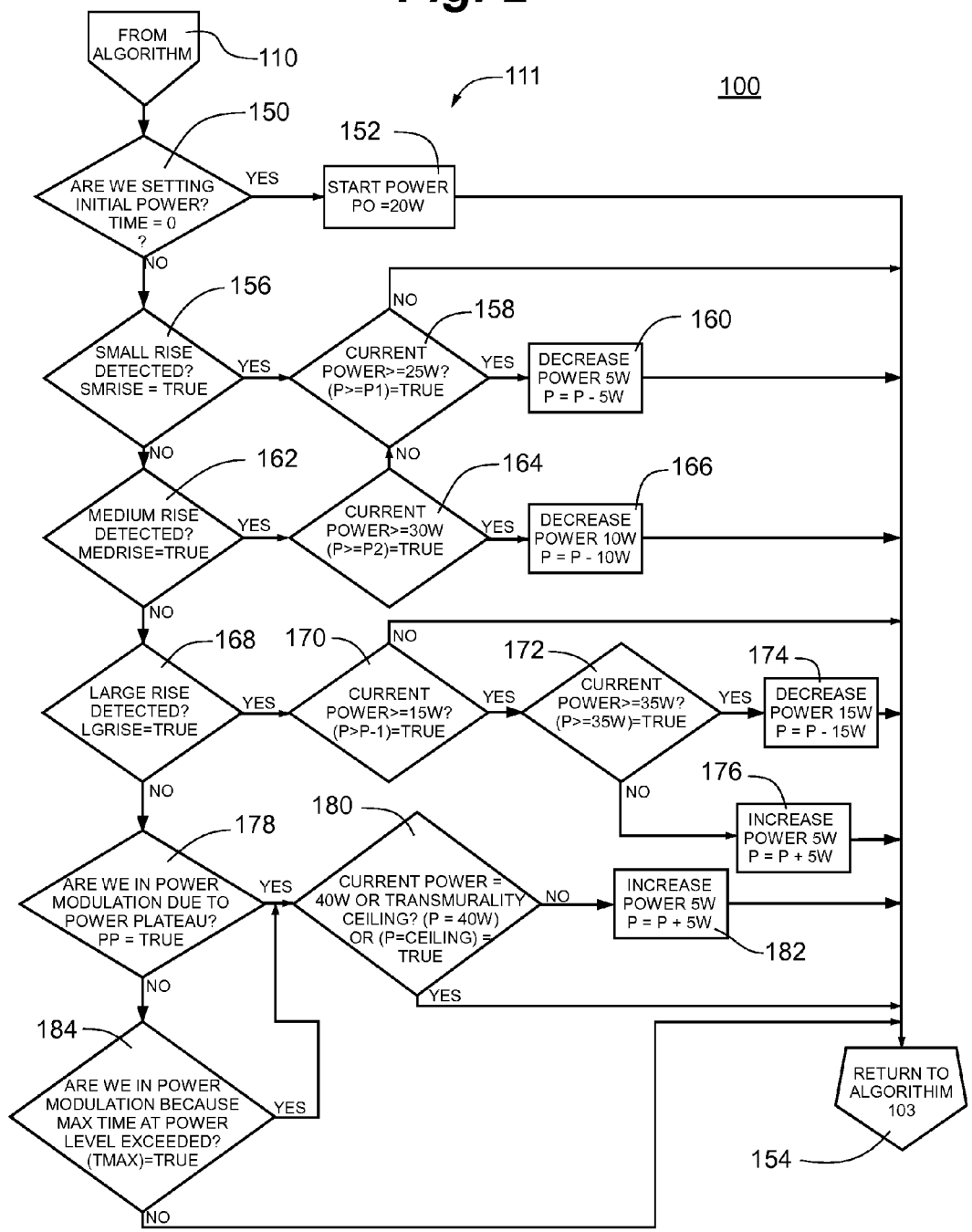
FIG. 2 is a flowchart depicting a power modulation algorithm according to one embodiment of the invention.

FIGS. 1 and 2 illustrate a method 100 of assessing transmurality of tissue being ablated and terminating delivery of ablation energy to an electrode in response to a plateau in impedance of the tissue in conjunction with a detected rise in impedance. The method 100 can be implemented during operation of an electrosurgical device to control the amount of ablation energy delivered by the device to the tissue and also to automatically terminate the delivery of ablation energy under certain conditions. The method 100 can be carried out by a controller having an electrical circuit or a software program, such as, for example, a microprocessor. The controller can be integrated into an electrosurgical device or electrically connected to the electrosurgical device. Data such as impedance measurements and temperature measurements that are used in the method 100 can be provided by sensors carried on the electrosurgical device. Likewise, the controller can be operably coupled to the output of the electrosurgical device to control the delivery of ablation energy to the electrode.

Figure 3:
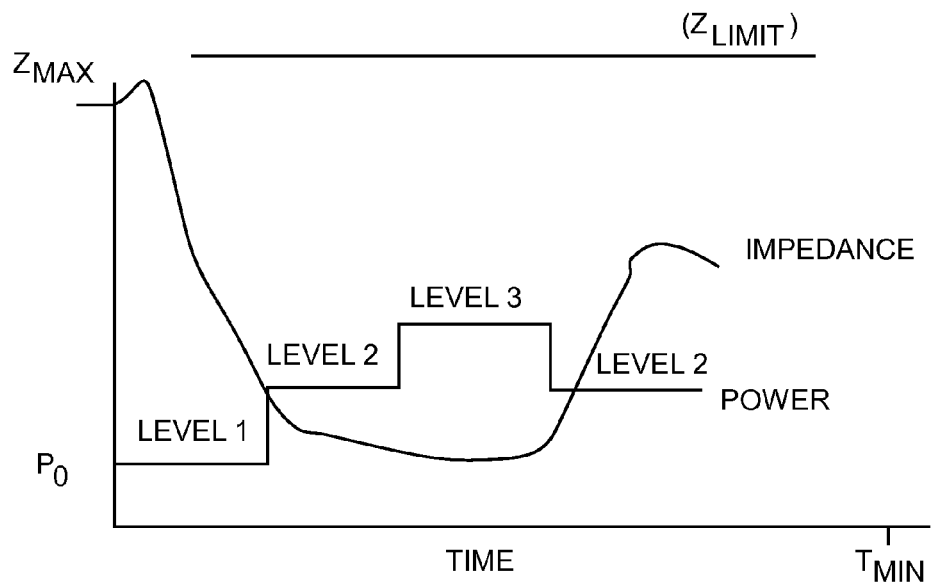
FIG. 3 is a chart illustrating an impedance versus power curve.

In general, the method 100 can monitor the tissue impedance profile or the impedance of the tissue being ablated as a function of time. During the early part of the ablation, the method 100 can gradually raise the power level of the ablation energy being delivered, while trying to detect a flattening of the tissue impedance profile. When a relatively flat impedance profile (or "power plateau") is discovered, the ablation power can be raised to a next level, as shown in FIG. 3. If there are no further changes in the tissue impedance profile (e.g., the impedance profile remains relatively flat after raising power in response to a power plateau), a transmurality plateau (TP) may be declared to exist. Transmurality, or the determination that the ablation procedure is complete (e.g., that the ablation extends through the thickness of the tissue to be ablated), may be indicated by any of several situations occurring, according to some embodiments of the invention. For example, if the total time of the ablation exceeds a minimum time delay ($T_{min}$) following a TP declaration, transmurality can be indicated. As another example, if the tissue impedance profile reaches an impedance limit ($Z_{limit}$) during ablation, transmurality can be indicated. As yet another example, if a rise in a certain parameter is detected (such as a rise in impedance or temperature), even if a TP has not been declared, and the rise occurs after a minimum total energy ($E_{min}$) has been delivered, transmurality can be indicated. Thus, embodiments of the invention provide a method of delivering an amount of energy to efficiently achieve a transmural ablation (e.g., reducing the time and/or energy expended to achieve a transmural ablation), while also minimizing the potential for over-ablation or tissue damage.

In order to prevent rapid impedance rises which can cause a high impedance shut off (HISO), for example, the method 100 can include a negative closed loop feedback system that can be kept active throughout the ablation. The negative closed loop feedback system can actively lower power output of the electrosurgical device if a rise in impedance is detected, according to some embodiments of the invention. The response of the closed loop feedback system may be based on how the rise in impedance is categorized, for example, according to one of three defined rise types. Thus, power can be actively modulated bi-directionally (e.g., positively or negatively) based on the slope of the impedance profile, for example, according to various embodiments of the invention.

Figure 4A:
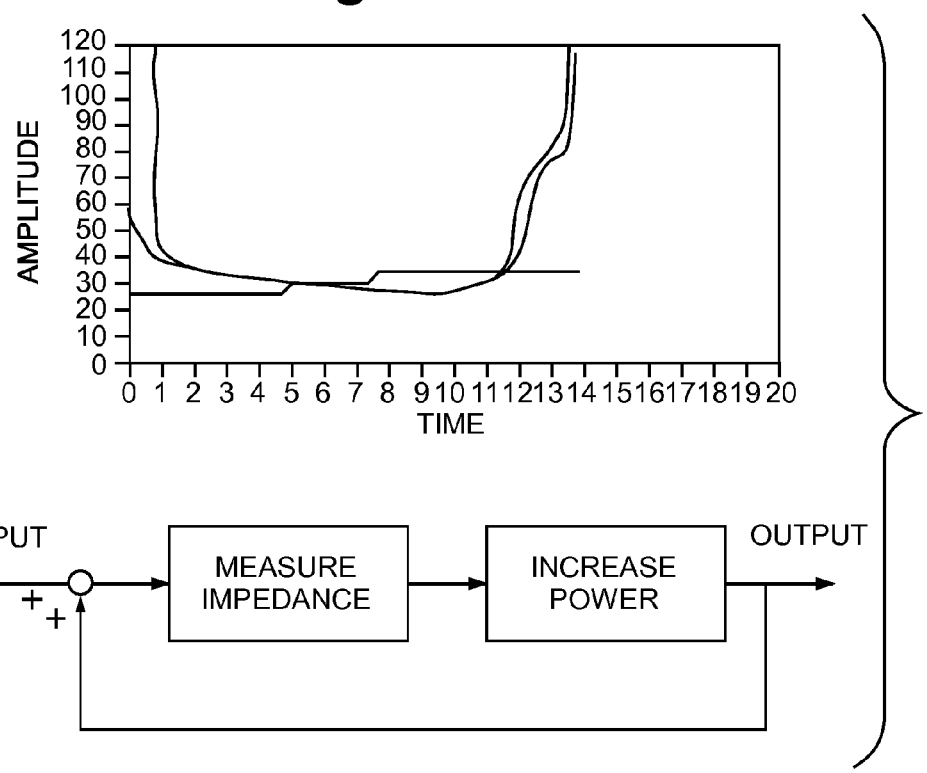
FIG. 4 includes two charts and two schematic diagrams illustrating an impedance profile and power output for positive closed loop feedback (a) and positive/negative closed loop feedback (b) systems.
Figure 4B:
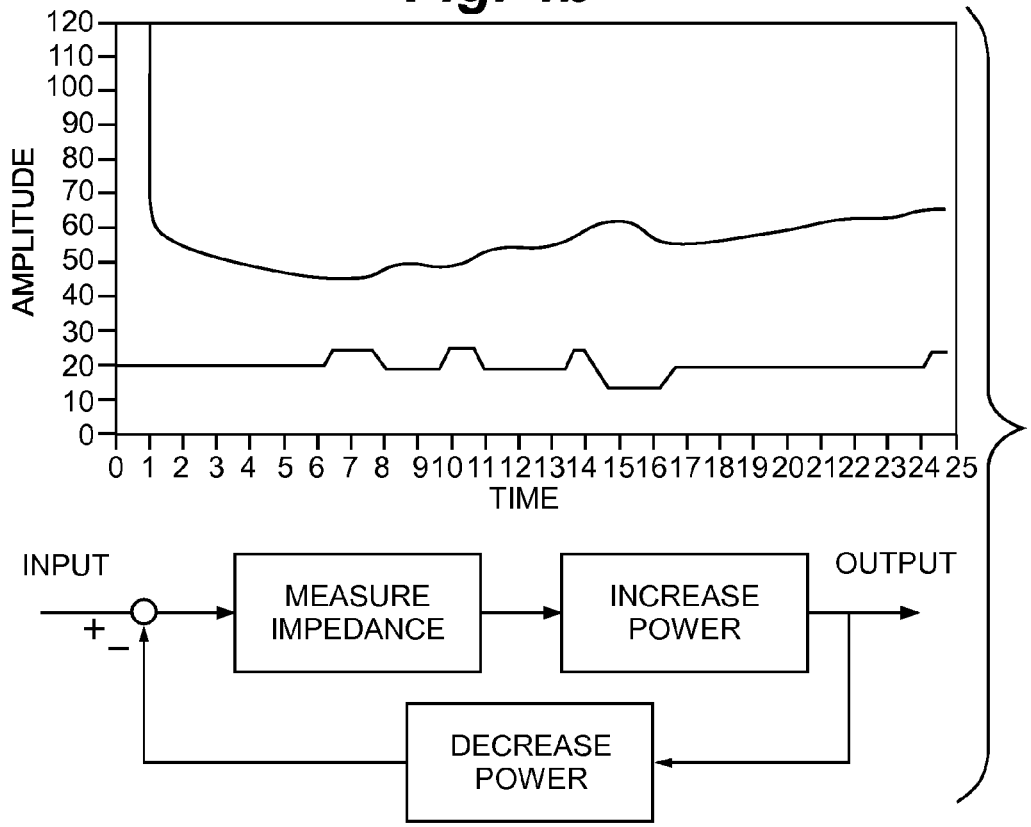

FIG. 4(a) illustrates an impedance profile and power level plot versus time of an algorithm for determining transmurality, in which power may only be increased (and not decreased) during the delivery of ablation energy. FIG. 4(b) illustrates a power level plot and resulting impedance profile of a method in accordance with some embodiments of the invention (such as method 100), in which power can be either increased or decreased as determined by the method.

Figure 5:
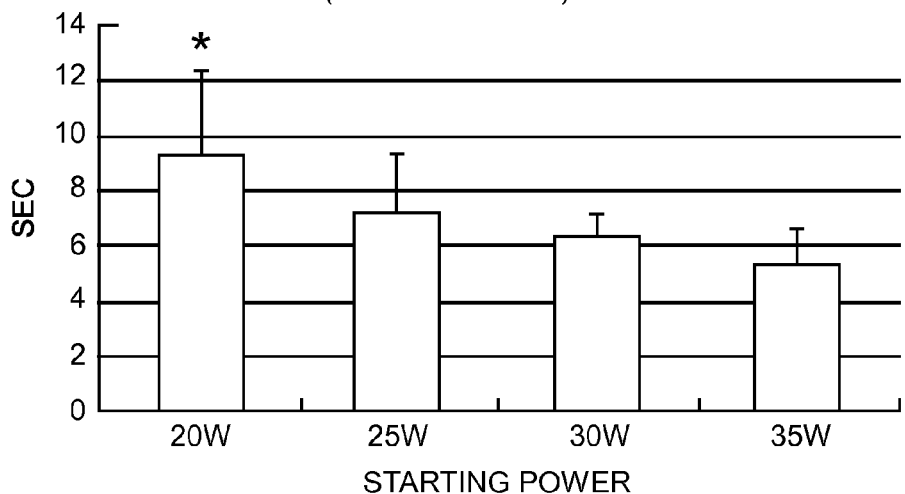
FIG. 5 is a chart illustrating a comparison of time to first power plateau for various starting powers.
Figure 6:
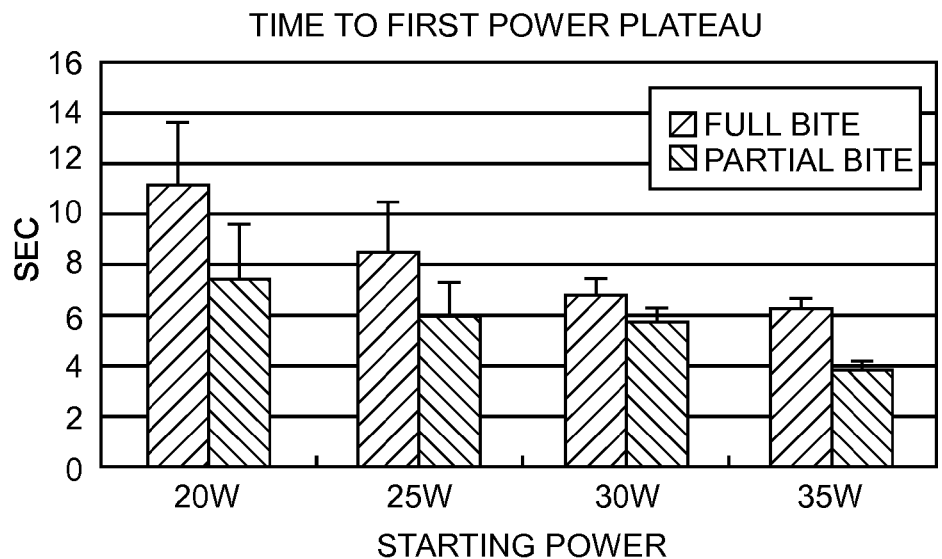
FIG. 6 is a chart illustrating a comparison of time to first power plateau for various starting powers broken down by full bite measurements (tissue along full length of electrode) and partial bite measurements (tissue along partial length of electrode).

As shown in FIG. 1, the ablation is initialized (at 102). A controller initiates delivery of ablation energy from an electrosurgical device to the tissue to be ablated and enters into a primary algorithm 103. The ablation energy may be delivered at a starting power, $P_0$. The starting power can contribute to an early impedance rise, which can occur within about ten seconds following the beginning of ablation. The starting power can also influence the rate of impedance decay until the impedance curve flattens, thus affecting overall ablation time. In some embodiments, the starting power, $P_0$, can be set to about 15 W, 20 W, 25 W, 30 W, or 35 W, as illustrated in FIGS. 5 and 6, or may be set to other values as deemed appropriate.

With continued reference to FIG. 1, the controller can determine (at 104) if a start-up blanking period has expired. The start-up blanking period, which can generally cover an initial ablation period, can be provided so that a sufficient number of measurements can be gathered before attempting to determine transmurality of an ablation lesion in tissue. The start-up blanking period can prevent erroneous data from previous ablations from being used in the analysis of the impedance profile and subsequent comparison to the criteria of plateaus (e.g., power plateaus and transmurality plateaus) and rise (e.g., impedance rise and temperature rise). The start-up blanking period can be set to start at t=0 during ablation (e.g., at the commencement of delivery of ablation energy to the tissue), and can have different lengths (e.g., it may be programmable and/or adjustable). In one possible embodiment, the start-up blanking period may be calculated using a formula that seeks to ensure sufficient data have been acquired prior to assessing transmurality. For example, the start-up blanking period may be defined as 1400+200*(y−1), wherein the start-up blanking period is a time period measured in milliseconds, and "y" is the number of dZ/dt calculations desired for making transmurality assessments. If the start-up blanking period has not yet expired, the controller can continue to deliver ablation energy at the starting power, for example. Once the start-up blanking period has expired, the controller can enter (at 106) a processing state in which a plurality of factors are processed or monitored in parallel with one another, while continuing to deliver ablation energy.

Figure 7:
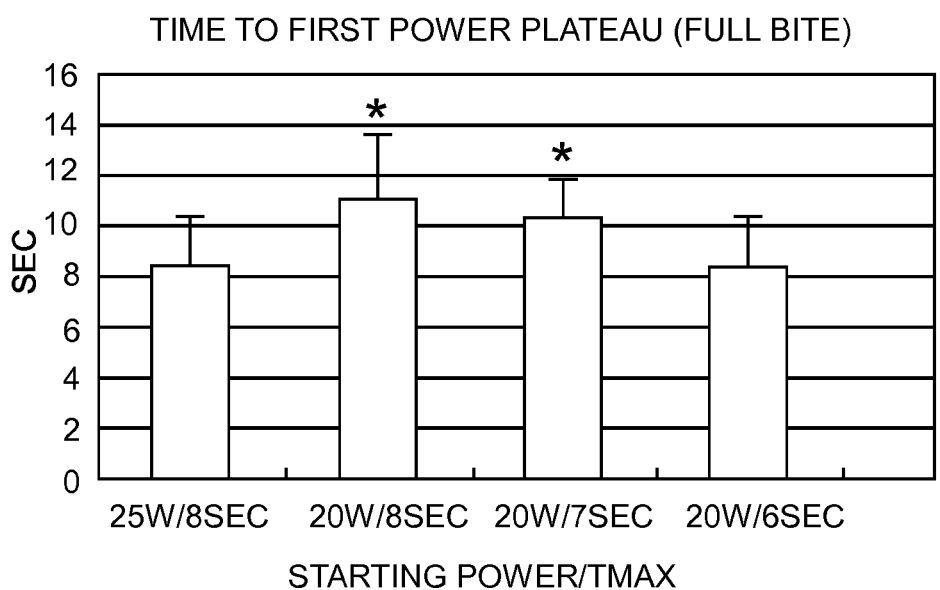
FIG. 7 is a chart illustrating a comparison of time to first power plateau for various maximum time values at a 20 W starting power.

Various embodiments of the invention may allow the power level of the ablation energy to be varied (e.g., increased or decreased). In some embodiments, a maximum time may be specified for delivery of ablation energy at each of a number of different power levels. Thus, with reference to FIG. 1, a first factor can determine (at 108) whether a maximum time, $t_{max}$, at the current power level has been exceeded. The value for $t_{max}$ can be the same for each power level, or it can differ depending upon the power level. Tables 1(a)-(c) below illustrate examples of $t_{max}$ values for each of several exemplary power levels according to embodiments of the invention. It should be noted that the particular values in Tables 1(a)-(c) are purely illustrative in nature; one of ordinary skill would be able to modify these values to achieve similar results without departing from the scope of the invention as claimed. FIG. 7 illustrates the impact of $t_{max}$ on the amount of time it can take to reach a first "power plateau." If $t_{max}$ has not been exceeded, no action is taken relative to the first factor. The controller can continue to deliver ablation energy and can remain (at 106) in the parallel processing state. If $t_{max}$ has been exceeded, the controller can exit (at 110) the primary algorithm 103 and can enter a power modulation algorithm 111, as shown in FIG. 2. This can ensure that the ablation energy is applied at a given power level for no longer than the maximum time ($t_{max}$) associated with that power level before the controller goes to the power modulation algorithm 111.

TABLE 1(a)

Power Levels and Times

| Level | Power (W) | Power plateau blanking period ($t_{min}$), seconds | Max time ($t_{max}$), seconds |
|---|---|---|---|
| $P_{-1}$ | 15 | 1.80 | 2.00 |
| $P_0$ | 20 | 1.80 | 6.00 |
| $P_1$ | 25 | 1.80 | 6.00 |
| $P_2$ | 30 | 1.80 | 6.00 |
| $P_3$ | 35 | 1.80 | 6.00 |
| $P_4$ | 40 | 1.80 | 35.00 |

TABLE 1(b)

Power Levels and Times

| Level | Power (W) | Power plateau blanking period ($t_{min}$), seconds | Max time ($t_{max}$), seconds |
|---|---|---|---|
| $P_{-1}$ | 20 | 2.00 | 4.0 |
| $P_0$ | 25 | 2.00 | 8.0 |
| $P_1$ | 30 | 2.00 | 8.0 |
| $P_2$ | 35 | 2.00 | 8.0 |
| $P_3$ | 40 | 2.00 | 8.0 |
| $P_4$ | 45 | 2.00 | 40.00 |

TABLE 1(c)

Power Levels and Times

| Level | Power (W) | Power plateau blanking period ($t_{min}$), seconds | Max time ($t_{max}$), seconds |
|---|---|---|---|
| $P_{-1}$ | 25 | 3.1 | 1.0 |
| $P_0$ | 30 | 3.1 | 5.00 |
| $P_1$ | 35 | 3.1 | 5.00 |
| $P_2$ | 40 | 3.1 | 5.00 |
| $P_3$ | 45 | 3.1 | 5.00 |
| $P_4$ | 50 | 3.1 | 30.00 |

As used above, a "power plateau," or flattened impedance profile, may occur during delivery of ablation energy to tissue. For example, the monitored impedance of the tissue being ablated is typically observed to decrease during delivery of ablation energy to tissue. At some point, the rate of decrease of the monitored impedance begins to level off (or flatten) during energy delivery. Such a power plateau may be indicated by a reduction in the absolute value of the slope of the monitored impedance during delivery of ablation energy, or by some comparable means of identifying a flattening of the impedance profile.

Figure 8:
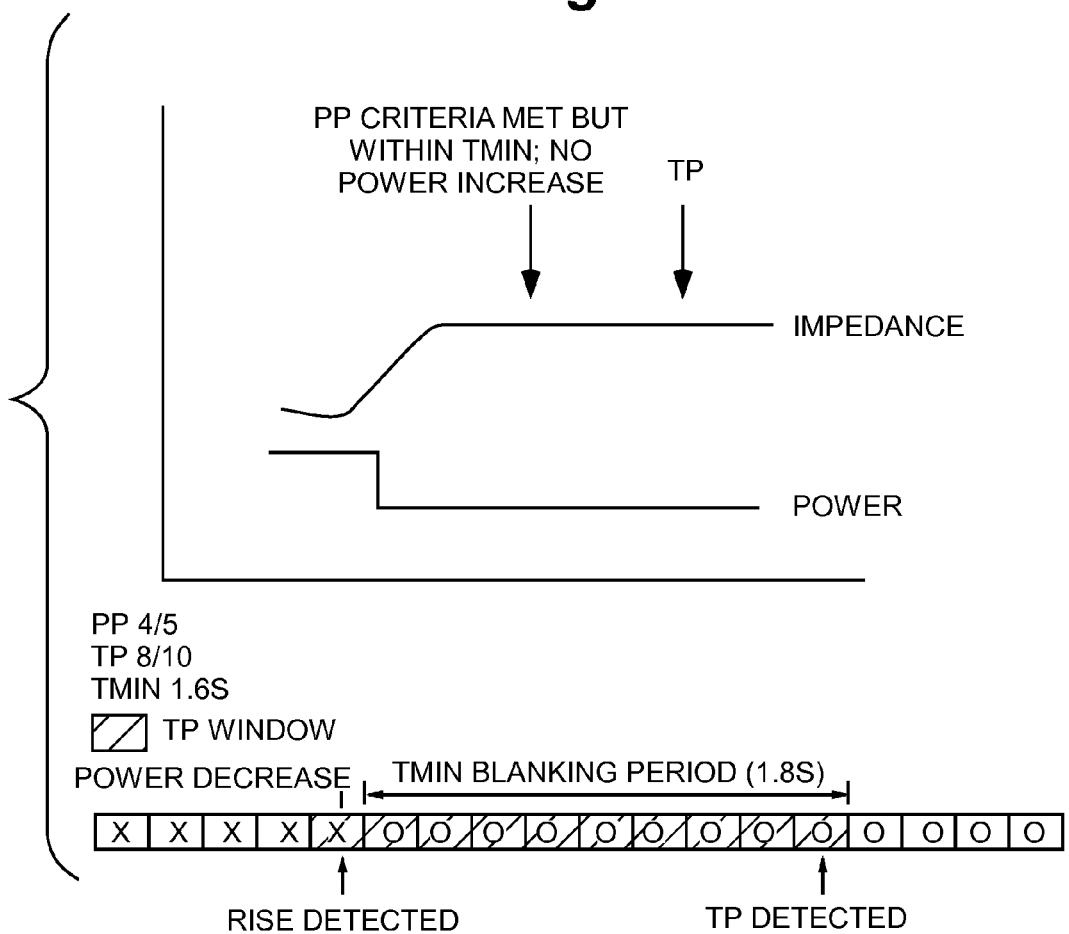
FIG. 8 includes two charts illustrating a situation where transmurality plateau is detected without a power increase.

A second factor can determine (at 112) whether a power plateau, or a flattened impedance profile, has been detected. If no power plateau has been detected, no action is taken relative to the second factor. The controller can continue to deliver ablation energy and can remain (at 106) in the parallel processing state. If a power plateau has been detected, the controller can determine (at 114) whether there has been a previous power decrease. If there has been a previous power decrease, the controller can go (at 110) to the power modulation algorithm 111. If there has not been a previous power decrease, the controller can determine (at 116) whether a power plateau blanking period or minimum time per power ($t_{min}$) has expired. The power plateau blanking period prevents excessive power increases from occurring within a short period of time. It also allows time so that tissue responds to a power change before another power change is applied. Unlike previous algorithms which did not provide a decrease power, an algorithm according to the method 100 allows power to decrease. This power decrement may lead to a possibility of TP detection without power ever having increased (as shown in FIG. 8). In order to prevent this problem, the power plateau blanking period, $t_{min}$, may not apply after a power decrement, according to some embodiments. This can also reduce the possibility of detecting a TP at a power level less than the starting power (i.e., $P_{-1}$). During the power plateau blanking period, the power is not increased, in some embodiments. Data collected during the power plateau blanking period can be used for decision making following expiration of the power plateau blanking period. In some embodiments, the power plateau blanking period, or $t_{min}$, can be about 1.8 seconds for each power level, according to the example shown above in Table 1.

If the power plateau blanking period (i.e., the minimum time at the current power level) has expired, the controller can go (at 110) to the power modulation algorithm 111 (FIG. 2). If the power plateau blanking period has not expired, no action is taken relative to the second factor. Again, this means that the controller can continue to deliver ablation energy and can return (at 106) to the parallel processing state.

Figure 9:
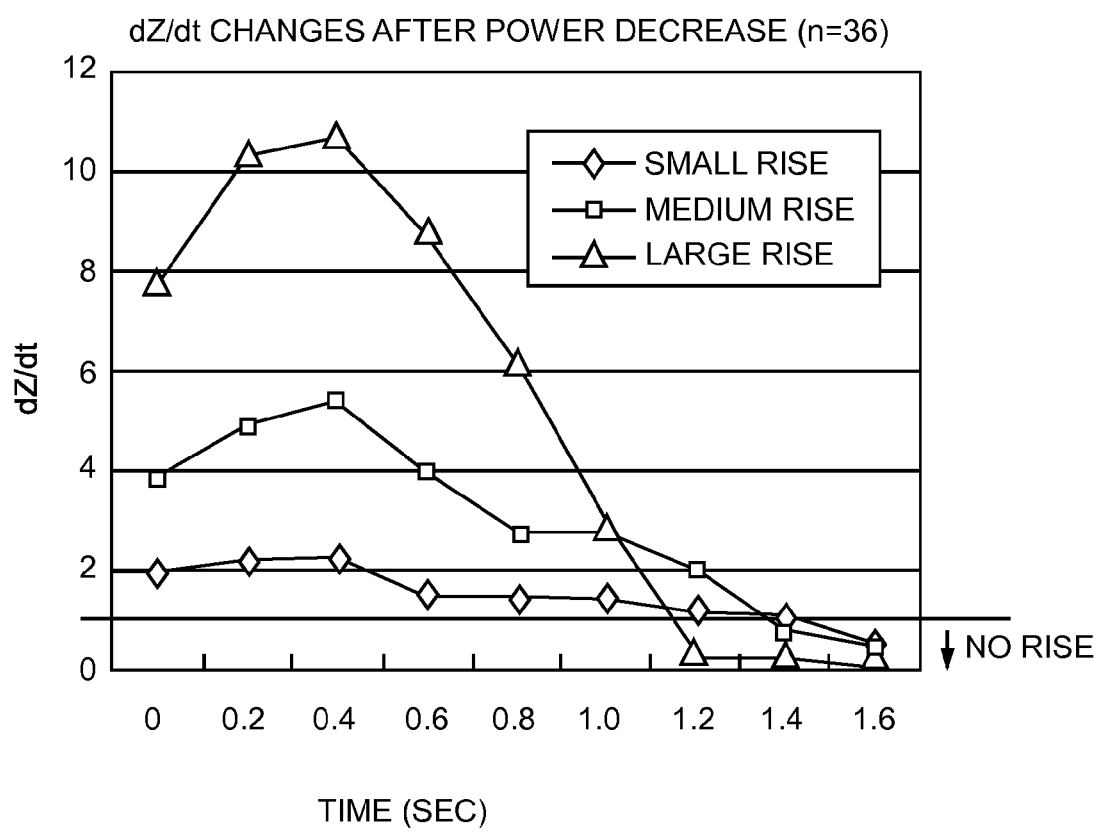
FIG. 9 is a chart illustrating a comparison of average dZ/dt value changes after a power decrease, with each rise (small, medium, and large rise) detected at t=0 seconds, and a dotted line indicating the boundary between no rise and small rise.

A third factor can determine (at 118) whether a rise has been detected. This can be an impedance rise or a temperature rise, for example. If no rise has been detected, no action is taken relative to the third factor. The controller can continue to deliver ablation energy and can remain (at 106) in the parallel processing state. If a rise has been detected, the controller can determine (at 120) whether a rise blanking period has expired. The rise blanking period can prevent excessive power increases due to the detection of multiple rises within a short period of time. The rise blanking period can also provide a minimum time so that impedance stabilizes after a power level change or modulation (as shown in FIG. 9). In some embodiments, the rise blanking period can be about 1.4 seconds. Data collected during the rise blanking period can be used for decision making following expiration of the rise blanking period.

If the rise blanking period has not yet expired, no action is taken relative to the third factor. The controller can continue to deliver ablation energy and can return (at 106) to the parallel processing state. If the rise blanking period has expired, the controller can determine (at 122) whether the total energy delivered by the electrosurgical device is greater than a minimum energy ($E_{min}$). Energy (Joules) is calculated as power (Watts)×time (seconds). For example, total energy can be calculated every 0.2 seconds as follows:

$$TotalEnergy(t = N \text{ sec}) = \sum_{n=1}^{5N} \frac{Power(n)}{5}$$

If the total energy delivered by the electrosurgical device is not greater than $E_{min}$, the controller can go (at 110) to the power modulation algorithm. If the total energy is greater than $E_{min}$, transmurality can be indicated (at 124) and the ablation (e.g., the delivery of ablation energy to a given tissue site) can be ended (at 126). $E_{min}$ can be selected to ensure that transmural lesions occur in every operating condition according to the algorithm of method 100. $E_{min}$ can be from about 300 J to about 500 J, in some embodiments.

A fourth factor can determine (at 128) whether the tissue impedance profile is greater than a maximum impedance ($Z_{limit}$). If the tissue impedance profile is less than or equal to $Z_{limit}$, no action is taken relative to the fourth factor. The controller can continue to deliver ablation energy and can remain (at 106) in the parallel processing state. If the tissue impedance profile is greater than $Z_{limit}$, transmurality can be indicated (at 124) and ablation can be ended (at 126).

A fifth factor can determine (at 130) whether the tissue impedance profile is greater than a high impedance shut off (HISO) limit. If the tissue impedance profile is not greater than the HISO limit, no action is taken relative to the fifth factor. This means that the controller can continue to deliver ablation energy and can remain (at 106) in the parallel processing state. If the tissue impedance profile is greater than the HISO limit, ablation can be ended (at 126) and an error report can be generated (at 132). The HISO limit can correspond to a safety limit of the tissue impedance profile. The fifth factor can limit the delivery of ablation energy regardless of the length of time ablation energy has been delivered, the power level of the ablation energy being delivered, or the indication of transmurality, etc.

As described above, a variety of conditions can cause the controller to exit the primary algorithm 103 and enter (at 110 in FIG. 1) the power modulation algorithm 111. FIG. 2 illustrates the power modulation algorithm 111. The power modulation algorithm 111 can be used to determine if and how to modulate the power level of the ablation energy, such as by increasing, decreasing, or maintaining the current power level.

Figure 10:
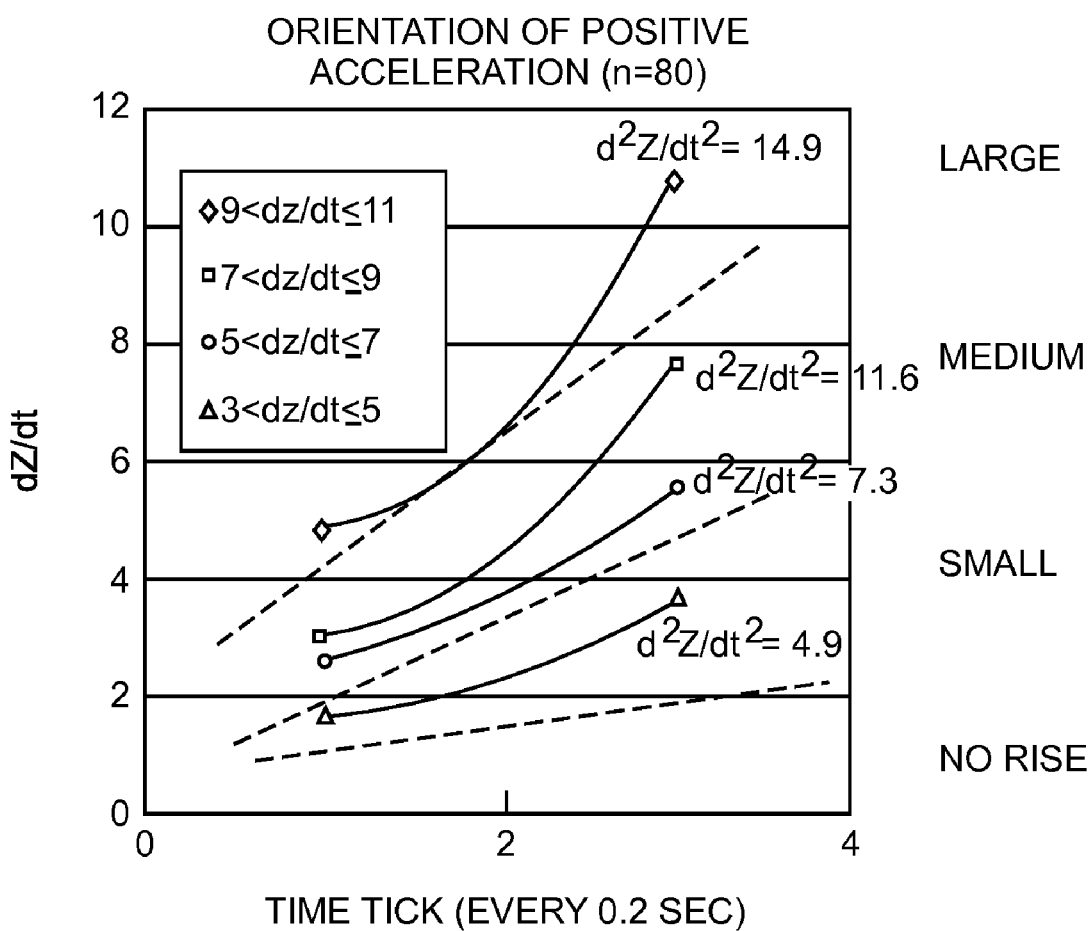
FIG. 10 is a chart illustrating a comparison of the direction of positive acceleration in different dZ/dt values, with dotted lines indicating boundaries between rise types.

As shown in FIG. 2, the controller can determine (at 150) if time is at zero, which corresponds to setting the starting power level. If time is not at zero, the starting power is set (at 152) and the controller can exit the power modulation algorithm 111 and return (at 154) to the primary algorithm 103. If the time is not zero, the controller can attempt to determine whether an impedance rise has been detected. A rise can be defined as a positive slope in the impedance profile, for example. In some embodiments, the impedance rise can be categorized according to the type of rise. For example, the magnitude of the slope may determine which type of impedance rise is occurring, including small, medium, and large impedance rises, as illustrated in FIG. 10. To determine the rise type, for example, a certain fraction of measured values (e.g., x out of y) must have a slope magnitude, dZ/dt, that exceeds a predetermined value, c. Tables 2(a) and 2(b) below provide exemplary values for x, y, and c for categorizing a rise in impedance as being a small, medium or large rise type. For example, using the criteria provided in Table 2(a), an impedance rise would be categorized as a "large" rise if 2 out of 4 measured values of impedance slope, dZ/dt, have a magnitude greater than 5.5.

TABLE 2(a)

| | Plateau Variables | | | | |
|---|---|---|---|---|---|
| Variable | Power plateau | Transmurality plateau | Rise small | Rise medium | Rise large |
| x | 4 | 9 | 3 | 2 | 2 |
| y | 5 | 10 | 5 | 4 | 4 |
| c | 1.3 | 1.3 | 1.3 | 3 | 5.5 |

For n = 1 to y; $\left[\frac{dZ}{dt}\right]_n > c$

TABLE 2(b)

| | Plateau Variables | | | | |
|---|---|---|---|---|---|
| Variable | Power plateau | Transmurality plateau | Rise small | Rise medium | Rise large |
| x | 6 | 13 | 4 | 3 | 3 |
| y | 7 | 14 | 7 | 6 | 6 |
| c | 1.5 | 1.5 | 1.5 | 3.1 | 6.8 |

In some embodiments, it may be desirable to further define a small rise as being, for example, 3 out of 5 measured values of impedance slope, dZ/dt, having a magnitude between 1.3 and 3 (e.g., the slope criteria for a medium rise). Similarly, it may be desirable in some embodiments to define a medium rise as being, for example, 2 out of 4 measured values of impedance slope, dZ/dt, having a magnitude between 3 and 5.5 (e.g., the slope criteria for a large rise).

If a small rise is detected (at 156), the controller can determine (at 158) if the current power is greater than a preset maximum corresponding to the small rise. In some embodiments, the preset small rise maximum power can be 25 W, for example. If the current power level is greater than or equal to the preset small rise maximum, power can be decreased (at 160) by a specified amount, for example, by 5 W. At that point, the controller may exit (at 154) the power modulation algorithm 111 and return to the primary algorithm 103. If the current power is less than the preset small rise maximum, the controller can exit (at 154) the power modulation algorithm 111 and can return to the primary algorithm 103 without modulating the power.

If a small rise is not detected (at 156), but a medium rise is detected (at 162), the controller can determine (at 164) if the current power is greater than a preset maximum corresponding to the medium rise. In one embodiment, the preset medium rise maximum power level is 30 W. If the current power is greater than or equal to the preset medium rise maximum, power can be decreased (at 166) by a certain amount, for example 10 W, and the controller can return (at 154) to the primary algorithm 103. If the current power is less than the preset medium rise maximum, the controller can return to the small rise determination (at 158) and can continue from there.

If a medium rise is not detected (at 162), but a large rise is detected (at 168), the controller can determine (at 170) if the current power level is greater than a preset minimum corresponding to the large rise. In one embodiment, the preset large rise minimum can be 15 W. If the current power is less than the preset large rise minimum, the controller can return (at 154) to the primary algorithm 103 without modulating the power. If the current power is greater than or equal to the preset large rise minimum, the controller can determine (at 172) if the current power is greater than or equal to a preset large rise maximum. If the current power is greater than or equal to the preset large rise maximum (e.g., 35 W), power can be decreased (at 174) by a certain amount, for example 15 W, and the controller can return (at 154) to the primary algorithm 103. If the current power is less than the preset large rise maximum, the controller can increase power (at 176) by a certain amount, for example 5 W, and can return (at 154) to the primary algorithm 103. In one embodiment, the preset large rise maximum can be 35 W.

Figure 11:
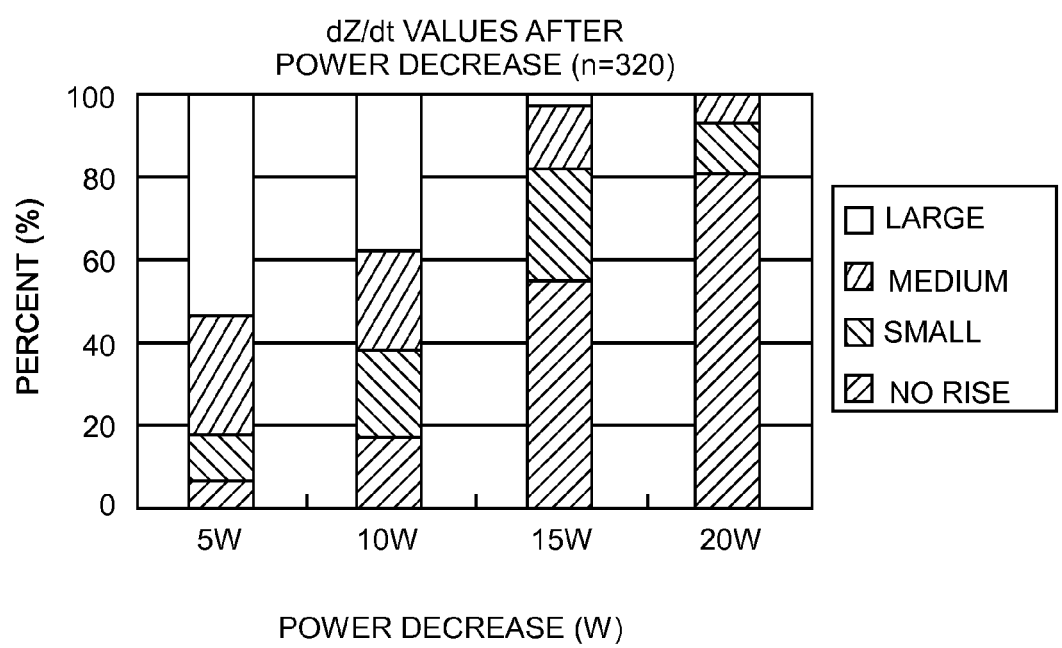
FIG. 11 is a chart illustrating a frequency plot of dZ/dt values at 1.4 seconds after a power decrement.

FIG. 11 illustrates a frequency plot of impedance slope (dZ/dt) values at 1.4 seconds after a power decrement. In FIG. 11, the dZ/dt values were categorized according to rise type (no rise, small, medium, and large rise), and the frequency of occurrence of each rise type is shown for each of the following power decrement amounts: 5 W, 10 W, 15 W, and 20 W. Table 3 below shows the decrement and minimum power level for each of the three rise types.

TABLE 3

Power decrement values and minimum power

| | Rise types | | |
|---|---|---|---|
| | Small | Medium | Large |
| Decrease amount | 5 watts | 10 watts | 15 watts |
| Minimum power level | $P_o$ | $P_o$ | $P_{-1}$ |

If none of a small, medium, or large rise is detected, the controller can determine (at 178) whether the power modulation algorithm 111 was entered due to a power plateau. If so, the controller can determine (at 180) if the current power is at a maximum power or the transmurality ceiling. In some embodiments, the maximum power can be a predetermined value, for example 40 W. If the current power level is either at the maximum power or at the transmurality ceiling, the controller can exit the power modulation algorithm 111 and can return (at 154) to the primary algorithm 103 without modulating the power. If the current power is not equal to either the maximum power or the transmurality ceiling, power can be increased (at 182) by a certain amount, for example 5 W, in some embodiments. The controller can then return (at 154) to the primary algorithm 103.

If none of a small, medium, or large rise has been detected and the power modulation algorithm 111 was not entered due to a power plateau, the controller can determine (at 184) if the power modulation algorithm 111 was entered because the maximum time ($t_{max}$) at a power level had been exceeded. If so, the controller can determine (at 180) if the current power is at a maximum power or the transmurality ceiling, substantially as described above. If not, the controller can return (at 154) to the primary algorithm 103.

Returning to FIG. 1, upon return (at 154) from the power modulation algorithm 111 to the primary algorithm 103, the controller returns (at 106) to the parallel processing state. In addition, concurrently with the controller entering the power modulation algorithm 111, the controller may also continue (at 186) with the primary algorithm 103.

The controller can determine (at 186) whether a transmurality plateau has been detected. If no transmurality plateau has been detected, the controller can return (at 106) to the parallel processing state. If a transmurality plateau has been detected, the controller may next determine (at 188) whether a minimum time per ablation ($T_{min}$) has expired. If $T_{min}$ has not expired, no further action is taken, the controller can continue to deliver ablation energy and can return (at 106) to the parallel processing state. If $T_{min}$ has expired, transmurality can be indicated (at 124) and ablation can be ended (at 126). The minimum time per ablation, $T_{min}$, can be about 10-30 seconds in some embodiments, as shown below in the exemplary groups of settings (Settings A-C) of Table 4, which also provides examples of other variable settings.

TABLE 4

Transmurality Mode Settings

| Variable | Description | Setting A | Setting B | Setting C |
|---|---|---|---|---|
| $t_1$ | Start time to check for $Z_{max}$ | 0.2 sec. | 0.3 sec. | 0.1 sec. |
| $t_2$ | Stop time to check for $Z_{max}$ | 2.0 sec. | 1.5 sec. | 2.2 sec. |
| $T_{max}$ | Maximum time per ablation | 40 sec. | 45 sec. | 50 sec. |
| $T_{min}$ | Minimum time per ablation | 19 sec. | 22 sec. | 24 sec. |
| $P_{max}$ | Maximum Power (watts) | 40 watts | 45 watts | 50 watts |
| Scale | Offset scale multiplier for $Z_{limit}$ | 2.8 | 3.0 | 2.5 |
| | Transmurality Shutoff: | Manual Shutoff | Manual Shutoff | Manual Shutoff |

In some embodiments, detection of a transmurality plateau can require that dZ/dt be greater than or equal to 1.3 for 9 out of 10 points in a detection window, as indicated in Table 2 (above). Requiring a significant number of the points in the detection window to satisfy the transmurality plateau criteria may ensure that there is only one power increment arising from the power modulation algorithm 111 in a transmurality plateau detection window.

To reduce the possibility of severe over-ablation, a maximum total ablation time ($T_{max}$) for creating an ablation lesion or for performing an ablation procedure can be imposed. In one embodiment, the maximum total ablation time is about 40 seconds, as indicated in the example shown in Table 4. When $T_{max}$ is reached, power delivery can be terminated regardless of the transmurality determination. In one embodiment, the controller may indicate an error condition to the user when power delivery is terminated due to maximum total ablation time, $T_{max}$, being reached. This indication can be an audible indicator, a visual indicator, or a combination of both.

In some embodiments, the tissue impedance (Z) can be measured or calculated about every 0.2 seconds, for example. However, in some circumstances, there can be a significant amount of noise in the signal. To reduce the effects of this noise, the data can be filtered. One example of a filtering method to reduce the effects of noise can be accomplished using a 5-point moving average of the measured impedance values:

$$Z = \left[\frac{Z_{t-2} + Z_{t-1} + Z_t + Z_{t+1} + Z_{t+2}}{5}\right]$$

The 5-point moving average may result in the filtered impedance lagging the measured impedance values by about 400 msec in embodiments in which impedance is measured or calculated every 200 msec, for example.

Figure 12:
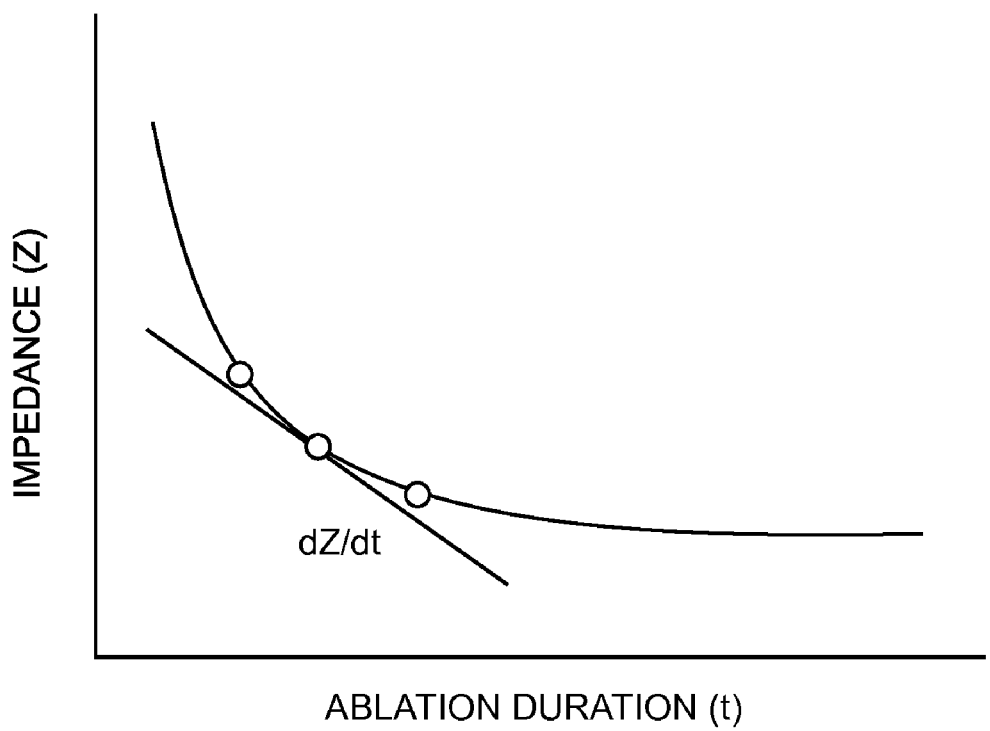
FIG. 12 is a chart illustrating a dZ/dt calculation.

The tissue impedance profile, or the rate of change in impedance per unit time (dZ/dt), can be calculated from the measured impedance values (e.g., without filtering), or from filtered impedance data (e.g., using the 5-point moving average), with a 3-point central difference algorithm, as shown in FIG. 12, and as described by the following equation:

$$\frac{dZ}{dt} = \frac{1}{2\Delta t}(Z_{t+1} - Z_{t-1})$$

The rate of change in impedance per unit time, dZ/dt, can therefore lag the filtered impedance by about 200 msec in some embodiments. To identify regions of the tissue impedance profile as a "rise" or a "plateau," a rolling window of dZ/dt points can be examined.

The method of assessing transmurality and terminating delivery of ablation energy to an electrode as described in relation to FIGS. 1 and 2 is based on the concept of finding a flat impedance profile or plateau. When the algorithm finds a flat impedance curve, it may raise power to a next level. If there are no further changes in the impedance profile, a transmurality plateau can be declared.

A plateau can be defined as a flattening of the impedance curve. To determine a plateau, the absolute value of a certain number (e.g., x out of y) of the dZ/dt points must be less than or equal to some defined slope value, c, wherein y is the number of points in the detection window:

$$\text{For } n = 1 \text{ to } y; \left|\frac{dZ}{dt}\right|_n \leq c$$

There are two types of plateaus—power plateaus and a transmurality plateaus—that may be defined, for example, by using different values for x and y, and having different responses (e.g., x out of y impedance slope values meeting certain criteria). Table 2 above shows examples of different criteria for identifying power and transmurality plateaus. When a power plateau is reached, the controller can increment the power level of the ablation energy to a next (e.g., higher) level. In some embodiments, a power plateau blanking period may also be established and used, whereby the criteria for identifying a power plateau is not evaluated until the completion of the power plateau blanking period. Such a power plateau blanking period may be employed, for example, following a change in power level of the ablation energy. When a transmurality plateau is reached, a transmurality flag can be set, and, in some embodiments, power cannot be increased beyond the power level at which the transmurality plateau was detected (e.g., the power level at which a transmurality plateau is identified may define a "ceiling" on the power level, or a "transmurality ceiling," according to some embodiments). Power can be allowed to be decreased and increased according to the power modulation criteria after a transmurality plateau is identified, but the ceiling cannot be exceeded, in some embodiments, as indicated at 180 in FIG. 2. When a transmurality plateau is detected at the same time that a power plateau is detected, the transmurality plateau rule may supersede the power plateau rule and power may remain at the same level, according to some embodiments of the invention.

The rise blanking period may be applied in certain situations. For example, in some embodiments, the rise blanking period is applied only in situations where a given rise (e.g., impedance rise or temperature rise) is of the same level (e.g., small, medium, or large) or below the level of a preceding rise. For example, the rise blanking period may apply between successive rises of equal type, or may apply when a medium rise occurs following a large rise, or when a small rise follows either a medium or a large rise.

Figure 13A:
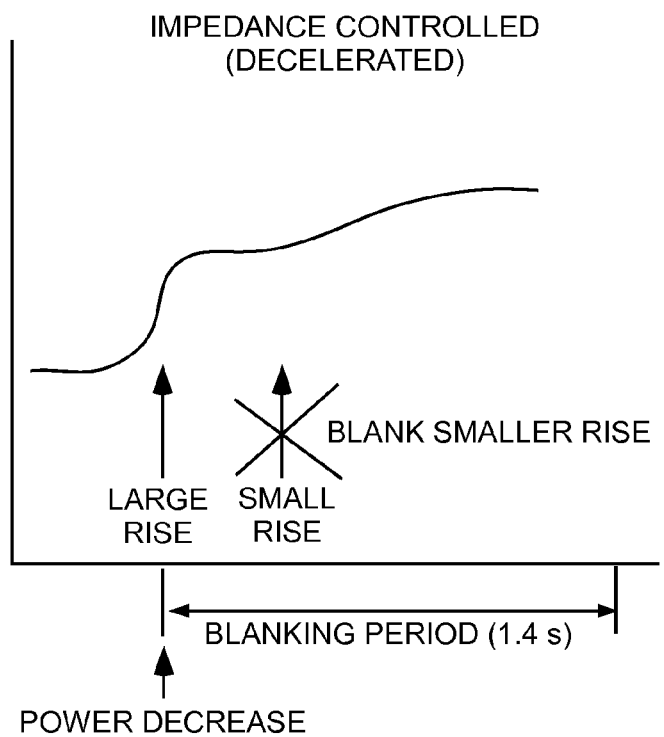
FIG. 13 is a chart illustrating an impedance profile in which a larger rise followed by a smaller rise is blanked (a), while a smaller rise followed by a larger rise is not blanked (b).
Figure 13B:
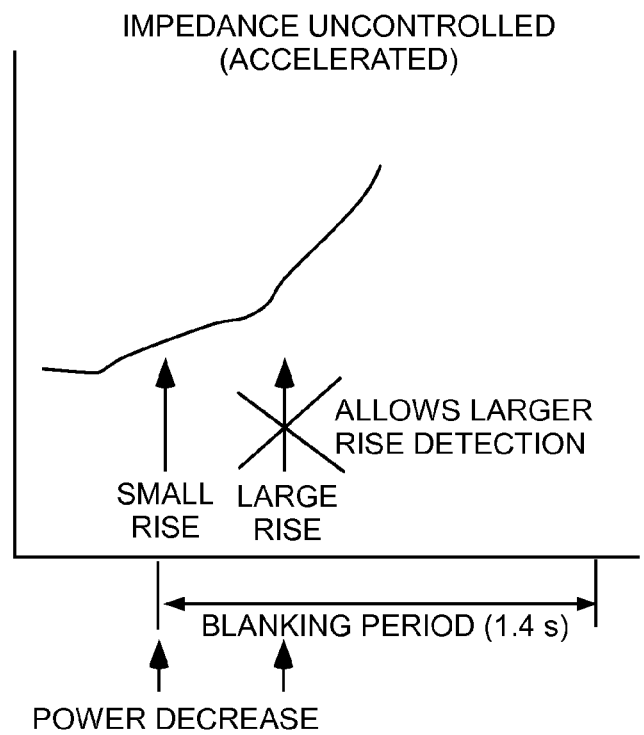

To further illustrate by way of example, if a medium rise is detected while ablating at 35 W, a 10 W reduction in power may be implemented according to the power modulation algorithm illustrated in FIG. 2. For the duration of the rise blanking period, or the next 1.4 seconds, while ablating at the reduced level of 25 W, the algorithm can be blanked from acting again on small or medium rises. This can allow time for the tissue impedance to stabilize and can reduce the rate of rise without overreacting and lowering power levels excessively. However, if a large impedance rise should be detected during the rise blanking period, the algorithm can immediately reduce power by 15 W or to a minimum power of 15 W, for example, regardless of the blanking period (e.g., the blanking period is ignored). FIG. 13 illustrates the application of the rise blanking period. In FIG. 13(a), a larger rise followed by a smaller rise is blanked, while in FIG. 13(b), a smaller rise followed by a larger rise is not blanked. If impedance is still rising after the rise blanking period expires, another power reduction can be implemented according to the algorithm of method 100.

Table 5 below provides a number of groups of exemplary settings and criteria (Settings A-C) that may be employed by a transmurality control algorithm according to some embodiments of the invention.

TABLE 5

Exemplary criteria and settings for the algorithm of FIGS. 1 and 2

|  | Setting A | Setting B | Setting C |
|---|---|---|---|
| Starting Power, $P_0$ | 20 W | 25 W | 30 W |
| Available Powers | 15, 20, 25, 30, 35 and 40 W | 20, 25, 30, 35, 40 and 45 W | 25, 30, 35, 40, 45 and 50 W |
| Power plateau criteria | 4/5 pts $\|dZ/dt\| = 1.3$ | 6/7 pts $\|dZ/dt\| = 1.5$ | 6/7 pts $\|dZ/dt\| = 1.5$ |
| $t_{max}$ (maximum time per power) | 6 sec 2 sec for $P_{-1} = 15$ W | 8 sec 4 sec for $P_{-1} = 20$ W | 5 sec 1 sec for $P_{-1} = 25$ W |
| $t_{min}$ (power plateau blanking period) | 1.8 sec | 2.0 sec | 3.1 sec |
| $T_{min}$ (minimum time per ablation) | 19 sec | 22 sec | 24 sec |
| Transmurality plateau | 9/10 pts $\|dZ/dt\| = 1.3$ | 13/14 pts $\|dZ/dt\| = 1.5$ | 13/14 pts $\|dZ/dt\| = 1.5$ |
| Rise criteria | three rise types: 3/5 pts dZ/dt > 1.3 (small), 2/4 pts dZ/dt > 3 (med), or 2/4 pts dZ/dt > 5.5 (large)) | three rise types: 4/7 pts dZ/dt > 1.5 (small), 3/6 pts dZ/dt > 3.1 (med), or 3/6 pts dZ/dt > 6.8 (large)) | three rise types: 4/7 pts dZ/dt > 1.5 (small), 3/6 pts dZ/dt > 3.1 (med), or 3/6 pts dZ/dt > 6.8 (large)) |
| Step down after rise detection | Small: by 5 W (no less than 20 W) Medium: by 10 W (no less than 20 W) Large: by 15 W (no less than 15 W) | Small: by 5 W (no less than 20 W) Medium: by 10 W (no less than 20 W) Large: by 15 W (no less than 15 W) | Small: by 5 W (no less than 20 W) Medium: by 10 W (no less than 20 W) Large: by 15 W (no less than 15 W) |
| After Rise detection | 1.4 sec blanking between rises of the same size; 1.4 sec blanking at med rise after large rise; 1.4 sec blanking at small rise after either med or large rise | 1.4 sec blanking between rises of the same size; 1.4 sec blanking at med rise after large rise; 1.4 sec blanking at small rise after either med or large rise | 1.4 sec blanking between rises of the same size; 1.4 sec blanking at med rise after large rise; 1.4 sec blanking at small rise after either med or large rise |
| Transmurality indication | Transmurality plateau and after $T_{min}$; $Z_{limit}$ reached; or Any type of rise after $E_{min} = 430$ J | Transmurality plateau and after $T_{min}$; $Z_{limit}$ reached; or Any type of rise after $E_{min} = 380$ J | Transmurality plateau and after $T_{min}$; $Z_{limit}$ reached; or Any type of rise after $E_{min} = 490$ J |
| Others | Ceiling: If TP declared, power level may be Modulated, but may not exceed the power level at the time of TP declaration | N/A | Ceiling: If TP declared, power level may be Modulated, but may not exceed the power level at the time of TP declaration |

In the method 100 of FIGS. 1 and 2, the occurrence of rapid impedance rises that might lead to a $Z_{limit}$ or to HISO condition have been reduced so that an ablation that fails to result in a TP will continue, running past $T_{min}$ and potentially all the way to $T_{max}$. However, the determination of the total amount of energy is used to provide an indication of transmurality in situations when a TP is not detected, thereby reducing instances in which ablation energy continues to be delivered until $T_{max}$. Energy provides a linear criteria in a relation of the formation of ablation lesions. The value for $E_{min}$ can be based on the maximum energy value which produces non-transmural lesions, along with an additional margin.

As shown below in Table 6, energy values from 340 J to 500 J with 20 J intervals at a fixed 20 W starting power can result in varying transmurality outcomes. In one example, reliable transmural lesions occurred with any value above 400 J using 20 W fixed power. The value 400 J is not necessarily, however, a minimum energy, since power can be reduced to $P_{-1}$, or the starting power decreased by one power step (i.e., 15 W). Therefore, a margin can be added so that 420 J can be a minimum energy value.

TABLE 6

Ablation results using fixed 20 W with various time

|  |  | Partial - Submerged (n = 72) | | Full - Submerged (n = 72) | |
|---|---|---|---|---|---|
| Energy (J) | Time (sec) | Trans (%) | Width (mm) | Trans (%) | Width (mm) |
| 340 | 17 | 31.2 | 2.3 ± 0.9 | 50.0 | 2.3 ± 1.2 |
| 360 | 18 | 56.3 | 2.2 ± 0.7 | 46.4 | 2.4 ± 1.2 |
| 380 | 19 | 100 | 2.3 ± 0.8 | 75.0 | 2.5 ± 1.1 |
| 400 | 20 | 100 | 2.4 ± 1.0 | 100 | 2.5 ± 1.0 |
| 420 | 21 | 100 | 2.4 ± 0.7 | 100 | 2.4 ± 1.2 |
| 440 | 22 | 100 | 2.5 ± 1.1 | 100 | 2.5 ± 1.1 |
| 460 | 23 | 100 | 2.9 ± 0.9 | 100 | 2.9 ± 0.9 |
| 480 | 24 | 100 | 2.9 ± 0.8 | 100 | 3.0 ± 10.7 |
| 500 | 25 | 100 | 2.9 ± 1.1 | 100 | 3.3 ± 0.8 |

Table 7 below illustrates transmurality outcomes for a fixed power value of 10 W to 40 W with 5 W intervals, using different timing to result in 420 J. As shown in Table 7, the powers above 20 W result in 100% transmurality.

TABLE 7

Ablation results of 420 J using various power and time

| Power (W) | Time (sec) | Partial - Submerged (n = 56) | | Full - Submerged (n = 56) | |
|---|---|---|---|---|---|
| | | Trans (%) | Width (mm) | Trans (%) | Width (mm) |
| 10 | 42 | 56.3 | 2.2 ± 1.0 | 46.4 | 2.1 ± 1.1 |
| 15 | 28 | 100 | 2.5 ± 0.8 | 75 | 2.4 ± 0.9 |
| 20 | 21 | 100 | 2.6 ± 0.7 | 100 | 2.5 ± 1.1 |
| 25 | 17 | 100 | 2.5 ± 0.7 | 100 | 2.6 ± 1.1 |
| 30 | 14 | 100 | 2.8 ± 0.9 | 100 | 2.8 ± 1.0 |
| 35 | 12 | 100 | 2.4 ± 1.2 | 100 | 2.9 ± 0.9 |
| 40 | 10.5 | 100 | 2.8 ± 0.8 | 100 | 3.3 ± 1.0 |

In some embodiments, the $E_{min}$ (minimum energy per ablation) value of 450 J can be set by adding 30 J of margin to the presumed minimum energy value (420 J). This minimum energy can be used to set a baseline for the transmural lesion. Therefore, the algorithm can indicate transmurality if there is any sign of impedance profile change (any type of rise detection) after total energy exceeds $E_{min}$.

The method 100 of FIGS. 1 and 2 performs particularly well on fat tissue. Since fat tissue includes little water, it has very high electrical resistivity. Therefore, the fat tissue can prevent RF current flow and can lead to a rapid impedance rise. This can cause termination of ablations due to $Z_{limit}$ or HISO without achieving transmurality. FIG. 14 illustrates test results using the algorithm of FIGS. 1 and 2, showing a high percentage of transmural ablation lesions, even in fat tissue.

The method 100 of FIGS. 1 and 2 can also reduce over-ablation. Compared to the previous algorithms, which maintained the power level at the time of a TP declaration, the method of FIGS. 1 and 2 may actively lower power when there is an impedance rise, for example. If there is excessive sizzling or a temperature rise, especially in thin tissue, the power level can be maintained between 15 W and 20 W, thus lowering the tissue temperature. Table 8 below shows that the rate at which sizzling occurs using the method 100 of FIGS. 1 and 2 to be lower than what would be expected using prior art techniques.

TABLE 8

In vitro testing results using method 100 of FIGS. 1 and 2

| | Time (sec) | Energy (Joules) | HISO (%) | $Z_{limit}$ (%) | Lesion width (mm) | Sizzle (%) | Transmurality (%) | End at $T_{min}$ (%) |
|---|---|---|---|---|---|---|---|---|
| Bovine (n = 120) | 19.0 ± 0.4 | 483 ± 53 | 0 | 1.7 | 2.6 ± 0.5 | 3.3 | 99.0 | 95.8 |
| Swine (n = 204) | 19.2 ± 1.4 | 447 ± 47 | 0 | 7.4 | 2.6 ± 0.5 | 4.4 | 99.0 | 85.3 |

Figure 15A:
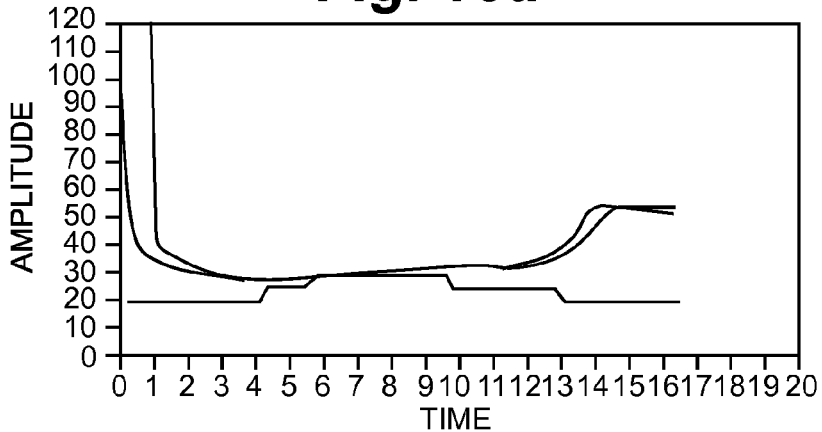
FIG. 15 includes two graphs illustrating the impedance profiles for a one rise step down algorithm according to one embodiment of the invention when rise is detected and either (a) power is decreased by 5 W or (b) power is decreased to zero.
Figure 15B:
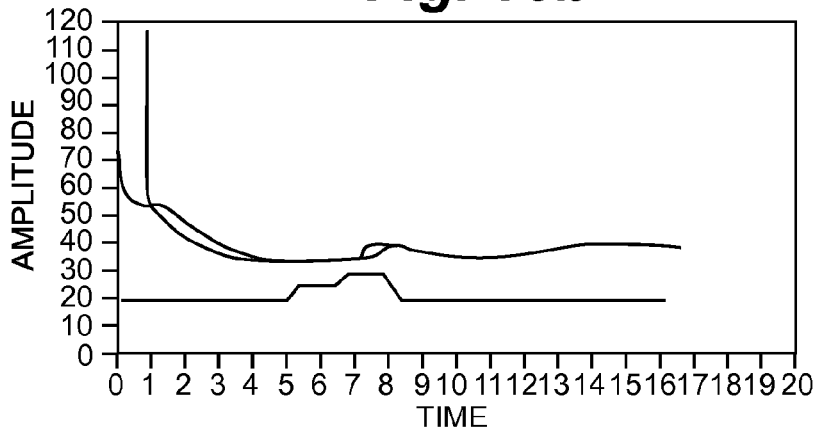

The power modulation algorithm 111 shown in FIG. 2 provides for the identification of three different rise types. However, this number can be increased or decreased. For example, the power modulation algorithm 111 can provide for the identification of one rise type. When a rise is detected, power can be lowered either by a pre-set amount, such as, for example, 5 W, or to the starting power, as shown in FIG. 15, and ablation can continue. The power modulation algorithm 111 can provide for the identification of two rise types, small and large. When a small rise is detected, power can be decreased by a pre-set amount, such as, for example, 5 W. When a large rise is detected, power can be decreased by a pre-set amount, such as, for example, 15 W, or to the starting power. Depending upon the number of rise types identified, various factors, including the maximum time ($T_{max}$) and the minimum time ($T_{min}$), can be adjusted accordingly.

Figure 16:
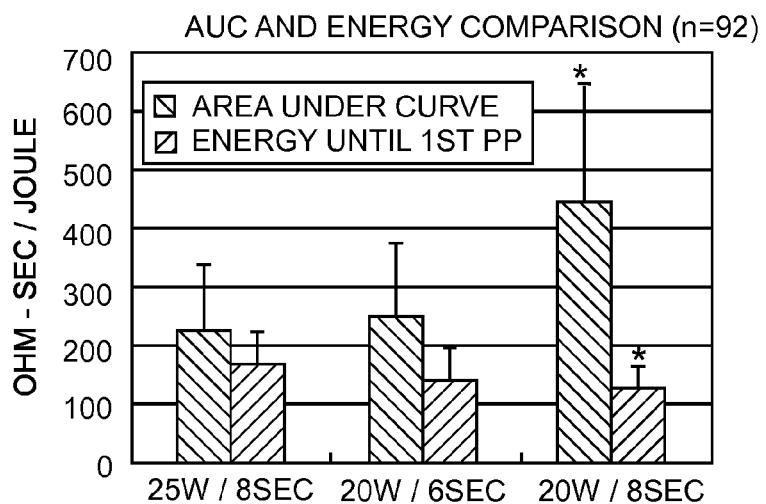
FIG. 16 is a chart illustrating a comparison of Area Under the Curve (AUC) and energy until transmurality plateau detection between different groups of starting power/$t_{max}$.

In FIG. 16, ablation performance until TP detection was compared using a starting power of 20 W, $t_{max}$ of 6 seconds, and PP criteria (4 out of 5 dZ/dt values >1.3). The area under the impedance curve (AUC) and energy values were compared. AUC can imply impedance decaying characteristics (slope and time), while energy can imply extent of power step up. The 20 W/6 second group shows smaller AUC but greater energy values compared to the 20 W/8 second group. This can indicate relatively faster impedance decaying while applying more power steps compared to 20 W/8 second group, which matches the 25 W/8 second group.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference in its entirety, as if each such patent or publication were individually incorporated by reference herein.

What is claimed is:

1. A method of applying ablation energy to achieve transmurality at a tissue site, the method comprising:
    applying ablation energy at a first power to the tissue site;
    monitoring, impedance of the tissue site;
    reducing the ablation energy applied to the tissue site to a second power in response to a rise in impedance; and
    reducing the ablation energy applied to the tissue site to a second power in response to a rise in impedance only if a rise blanking period has been met.

2. A method of applying ablation energy to achieve transmurality at a tissue site, the method comprising:
    applying ablation energy at a first power to the tissue site
    monitoring impedance of the tissue site;
    reducing the ablation energy applied tissue site to a second power in response to a rise in impedance; and
    monitoring total ablation energy and terminating delivery of ablation energy if the total ablation energy exceeds a preset minimum following a rise in impedance.

3. A method of applying ablation energy to achieve transmurality at a tissue site. the method comprising:
    applying ablation energy at a first power to the tissue site;
    monitoring impedance of the tissue site;
    reducing the ablation energy applied to the tissue site to a second power in response to a rise in impedance; and
    determining a rate of increase in impedance and assigning the rate of increase in impedance to one of at least three levels.

4. The method of claim 3, wherein the second power is selected based on the assigned level.

5. A method of applying ablation energy to achieve transmurality at a tissue site, the method comprising:
applying ablation energy at a first power to the tissue site monitoring impedance of the tissue site;
reducing the ablation energy a lied to the tissue site second power in response to a rise in impedance; and
indicating transmurality in response to detecting a rise in the monitored impedance of the tissue site occurring after a minimum total energy, $E_{min}$, has been delivered.

6. A method of applying ablation energy to achieve transmurality at a tissue site, the method comprising:
applying ablation energy at a first power to the tissue site;
monitoring impedance of the tissue site;
reducing the ablation energy applied to the tip sue site to a second power in response to a rise in impedance; and
indicating transmurality in response to detecting a rise in a temperature of the tissue site occurring after a minimum total energy, $E_{min}$, has been delivered.

7. A method of applying ablation energy to achieve transmurality at a tissue site, the method comprising:
applying ablation energy at a first power to the tissue site;
monitoring impedance of the tissue site;
increasing the ablation energy applied to the tissue site to a second power in response to a rise in impedance; and
increasing the ablation energy applied to the tissue site to a third power in response to a power plateau only if ablation energy has been applied to the tissue site at the second power for a minimum time.

8. A method of applying ablation energy to achieve transmurality at a tissue site, the method comprising:
applving ablation energy at a starting power level to the tissue site;
monitoring an impedance of the tissue site;
increasing the ablation energy applied to the tissue site to a second power level in response to at least one of detection of a power plateau and application of the ablation energy at the starting power level for a minimum time;
reducing the ablation energy applied to the tissue site to a third power level in response to an increase in the impedance of the tissue site; and
indicating transmuralitv in response to a transmurality plateau following a rise in impedance;
wherein the ablation energy applied to the tissue site is increased to the second power level only after ablation energy has been applied at the starting power level for the minimum time; and
wherein the minimum time applies only if the starting power level has been previously decreased.

9. A method of applying ablation energy to achieve transmurality at a tissue site, the method comprising:
applying ablation energy at a starting level to the tissue site;
monitoring an impedance of the tissue site;
increasing the ablation energy applied to the tissue site to a second power level in response to at least one of detection of a power plateau and application of the ablation energy at the starting power level for a minimum time;
reducing the ablation energy applied to the tissue site to a third power level in response to an increase in the impedance of the tissue site;
indicating transmurality in response to a transmurality plateau following a rise in impedance; and
monitoring total ablation energy delivered, and indicating transmurality if the total ablation energy delivered exceeds a preset minimum following the rise in impedance.

10. A method of applying ablation energy to achieve transmurality at a tissue site, the method comprising:
applying ablation energy at a starting power level to the tissue site;
monitoring an impedance of the tissue site;
increasing the ablation energy applied to the tissue site to a second power level in response to at least one of detection of a power plateau and application of the ablation energy at the starting power level for minimum time;
reducing the ablation energy applied tissue site to a third power level in response to an increase in the impedance of the tissue site;
indicating transmurality in response to a transmurality plateau following a rise in impedance; and
deteimining a rate of increase in impedance and assigning the rate of increase in impedance to one of at least three levels.

11. The method of claim 10, wherein the reduction in power is selected based on the assigned level.

12. A. system for assessing transmurality of an ablation procedure being at a tissue site. the system comprising:
a sensor that determines impedance of the tissue site;
a controller adapted to communicate with the sensor to monitor the impedance of the tissue site;
the controller being adapted to increase ablation energy applied to the tissue site to a second power level in response to at least one of detection by the sensor of a power plateau and application of ablation energy at a first power level for a minimum time;
the controller being adapted to reduce ablation energy applied to the tissue site to a third power level in response to an increase in impedance of the tissue site;
the controller being further adapted to indicate transmurality in response to a transmurality plateau following a rise in impedance of the tissue site; and
wherein the controller indicates transmurality in response to a total ablation energy provided exceeding a preset minimum following a rise in impedance.

* * * * *

UNITED STATES PATENT AND TRADEMARK OFFICE
CERTIFICATE OF CORRECTION

PATENT NO. : 7,959,626 B2
APPLICATION NO. : 11/780911
DATED : June 14, 2011
INVENTOR(S) : Jinback Hong, David E. Francischelli and Mark T. Stewart It is certified that error appears in the above-identified patent and that said Letters Patent is hereby corrected as shown below:

Column 16 Line 30 Error reads as "monitoring, impedance";
should read as "monitoring impedance"

Column 16 Line 59 Error reads as "tissue site. the method";
should read as "tissue site, the method"

Column 17 Line 17 Error reads as "energy a lied";
should read as "energy applied"

Column 17 Line 16 Error reads as "to the tip sue site";
should read as "to the tissue site"

Column 18 Line 35 Error reads as "tissue site. the system";
should read as "tissue site, the system"

Signed and Sealed this
Twenty-fifth Day of October, 2011

David J. Kappos
*Director of the United States Patent and Trademark Office*